United States Patent
Baarman et al.

(10) Patent No.: US 8,138,875 B2
(45) Date of Patent: *Mar. 20, 2012

(54) INDUCTIVELY POWERED APPARATUS

(75) Inventors: David W. Baarman, Fennville, MI (US); Stephen J. McPhilliamy, Chicago, IL (US); Christopher Houghton, Chicago, IL (US)

(73) Assignee: Access Business Group International LLC, Ada, MI (US)

( * ) Notice: Subject to any disclaimer, the term of this patent is extended or adjusted under 35 U.S.C. 154(b) by 212 days.

This patent is subject to a terminal disclaimer.

(21) Appl. No.: 12/612,996

(22) Filed: Nov. 5, 2009

(65) Prior Publication Data

US 2010/0072826 A1   Mar. 25, 2010

Related U.S. Application Data

(60) Continuation of application No. 11/468,149, filed on Aug. 29, 2006, now Pat. No. 7,639,110, which is a division of application No. 11/036,688, filed on Jan. 14, 2005, now Pat. No. 7,233,222, which is a division of application No. 10/357,932, filed on Feb. 4, 2003, now Pat. No. 7,126,450, which is a continuation-in-part of application No. 10/133,860, filed on Apr. 26, 2002, now Pat. No. 6,731,071, which is a continuation-in-part of application No. 09/592,194, filed on Jun. 12, 2000, now Pat. No. 6,439,299, said application No. 10/357,932 is a continuation-in-part of application No. 10/246,155, filed on Sep. 18, 2002, now Pat. No. 6,825,620, which is a continuation-in-part of application No. 10/175,095, filed on Jun. 18, 2002, now Pat. No. 6,673,250, which is a continuation-in-part of application No. 09/592,194, and a continuation-in-part of application No. 29/165,043, filed on Aug. 2, 2002, now Pat. No. Des. 476,095, and a continuation-in-part of application No. 29/165,008, filed on Aug. 2, 2002, now Pat. No. Des. 479,356, and a continuation-in-part of application No. 29/165,012, filed on Aug. 2, 2002, now Pat. No. Des. 476,094, and a continuation-in-part of application No. 29/165,005, filed on Aug. 2, 2002, now Pat. No. Des. 479,892, and a continuation-in-part of application No. 29/165,009, filed on Aug. 2, 2002, now Pat. No. Des. 475,471, and a continuation-in-part of application No. 29/165,011, filed on Aug. 2, 2002, now Pat. No. Des. 478,834.

(60) Provisional application No. 60/140,159, filed on Jun. 21, 1999, provisional application No. 60/140,090, filed on Jun. 21, 1999.

(51) Int. Cl.
*H01F 21/00* (2006.01)
(52) U.S. Cl. ........................................ 336/121; 336/122
(58) Field of Classification Search .................. 336/121, 336/122, 123, 126, 125, 124; 315/276, 274, 315/275, 277
See application file for complete search history.

(56) References Cited

U.S. PATENT DOCUMENTS

| | | |
|---|---|---|
| 602,966 A | 4/1898 | Wallach |
| 723,836 A | 3/1903 | Cowing |
| 843,534 A | 2/1907 | Hewitt |
| 1,137,333 A | 4/1915 | Klorer |
| 1,604,870 A | 10/1926 | Asman |
| 1,808,571 A | 5/1931 | Ulman |
| 1,852,740 A | 4/1932 | Doane |
| 2,199,107 A | 4/1940 | Kibbe |
| 2,265,475 A | 12/1941 | Fodor |
| 2,358,063 A | 7/1944 | Otis |
| 2,686,866 A | 8/1954 | Williams |
| 2,726,116 A | 12/1955 | Barber |
| 2,731,547 A | 1/1956 | Callard |
| 3,047,765 A | 7/1962 | Vichill |
| 3,292,579 A | 12/1966 | Buchanan |
| 3,550,682 A | 12/1970 | Fowler |
| 3,551,091 A | 12/1970 | Veloz |
| 3,628,086 A | 12/1971 | Nuckolls |
| 3,641,336 A | 2/1972 | Boin |
| 3,662,460 A | 5/1972 | Daley |
| 3,743,989 A | 7/1973 | Nicolas et al. |
| 3,746,906 A | 7/1973 | Cardwell, Jr. |
| 3,867,661 A | 2/1975 | Waltz et al. |
| 3,885,185 A | 5/1975 | Tilley |
| 3,885,211 A | 5/1975 | Gutai |
| 3,923,663 A | 12/1975 | Reid |
| 3,938,018 A | 2/1976 | Dahl |

| | | | | | | |
|---|---|---|---|---|---|---|
| 4,005,330 A | 1/1977 | Glascock, Jr. et al. | | 5,455,467 A | 10/1995 | Young et al. |
| 4,010,400 A | 3/1977 | Hollister | | 5,465,025 A | 11/1995 | Hendrickson |
| 4,017,764 A | 4/1977 | Anderson | | 5,504,399 A | 4/1996 | Tobler |
| 4,038,625 A | 7/1977 | Tompkins et al. | | 5,506,560 A | 4/1996 | Takeuchi et al. |
| 4,076,996 A | 2/1978 | Maehara et al. | | 5,536,979 A | 7/1996 | McEachern et al. |
| 4,093,893 A | 6/1978 | Anderson | | 5,550,452 A | 8/1996 | Shirai et al. |
| 4,101,777 A | 7/1978 | Reid | | 5,553,312 A | 9/1996 | Gattey et al. |
| 4,117,378 A | 9/1978 | Glascock, Jr. | | 5,594,304 A | 1/1997 | Graber |
| 4,160,193 A | 7/1979 | Richmond | | 5,596,567 A | 1/1997 | deMuro et al. |
| 4,282,563 A | 8/1981 | Ohta et al. | | 5,600,225 A | 2/1997 | Goto |
| 4,287,809 A | 9/1981 | Egli et al. | | 5,611,918 A | 3/1997 | Markham |
| 4,300,073 A | 11/1981 | Skwirut et al. | | 5,619,182 A | 4/1997 | Robb |
| 4,367,434 A | 1/1983 | Miller | | 5,653,531 A | 8/1997 | Yang |
| 4,389,595 A | 6/1983 | Kamei et al. | | 5,675,677 A | 10/1997 | Davenport et al. |
| 4,414,489 A | 11/1983 | Young | | 5,680,028 A | 10/1997 | McEachern |
| 4,434,388 A | 2/1984 | Carver et al. | | 5,716,126 A | 2/1998 | Meyer |
| 4,547,705 A | 10/1985 | Hirayama et al. | | 5,734,254 A | 3/1998 | Stephens |
| 4,556,837 A | 12/1985 | Kobayashi et al. | | 5,737,211 A | 4/1998 | Hirai et al. |
| 4,584,707 A | 4/1986 | Goldberg et al. | | 5,747,894 A | 5/1998 | Hirai et al. |
| 4,615,799 A | 10/1986 | Mortensen | | 5,771,438 A | 6/1998 | Palermo et al. |
| 4,637,434 A | 1/1987 | Moen | | 5,781,287 A | 7/1998 | Heinzl et al. |
| 4,638,250 A * | 1/1987 | Shen-Orr et al. ........ 324/207.17 | | 5,796,334 A | 8/1998 | Chen et al. |
| 4,675,573 A | 6/1987 | Miram et al. | | 5,814,900 A | 9/1998 | Esser et al. |
| 4,675,638 A | 6/1987 | Szabo | | 5,831,348 A | 11/1998 | Nishizawa |
| 4,747,158 A | 5/1988 | Goldberg et al. | | 5,831,516 A | 11/1998 | Jennings |
| 4,752,401 A | 6/1988 | Bodenstein | | 5,834,905 A | 11/1998 | Godyak et al. |
| 4,754,180 A | 6/1988 | Kiedrowski | | 5,903,207 A | 5/1999 | Lampe, Jr. et al. |
| 4,762,613 A | 8/1988 | Snowball | | 5,905,343 A | 5/1999 | McCamant |
| 4,772,991 A | 9/1988 | Wood | | 5,913,820 A | 6/1999 | Bladen et al. |
| 4,779,068 A | 10/1988 | Sakamoto et al. | | 5,923,544 A | 7/1999 | Urano |
| 4,780,803 A | 10/1988 | Garcia-Santamaria | | 5,928,505 A | 7/1999 | Inakagata et al. |
| 4,800,328 A | 1/1989 | Bolger et al. | | 5,929,598 A | 7/1999 | Nakama et al. |
| 4,812,702 A | 3/1989 | Anderson | | 5,949,155 A | 9/1999 | Tamura et al. |
| 4,816,977 A | 3/1989 | Sorensen | | 5,951,155 A | 9/1999 | Lanser |
| 4,818,855 A | 4/1989 | Mongeon et al. | | 5,952,814 A | 9/1999 | VanLerberghe |
| 4,838,797 A | 6/1989 | Dodier | | 5,963,012 A | 10/1999 | Garcia et al. |
| 4,854,214 A | 8/1989 | Lowe | | 5,980,056 A | 11/1999 | West |
| 4,857,204 A | 8/1989 | Joklik | | 5,990,611 A | 11/1999 | Lee |
| 4,894,591 A | 1/1990 | Witting | | 6,005,304 A | 12/1999 | Seelig |
| 4,933,606 A | 6/1990 | Tary | | 6,020,682 A | 2/2000 | Holzer |
| 4,939,494 A | 7/1990 | Masuda et al. | | 6,027,225 A | 2/2000 | Martin et al. |
| 4,954,756 A | 9/1990 | Wood et al. | | 6,028,413 A | 2/2000 | Brockmann |
| 4,958,266 A | 9/1990 | Sorensen et al. | | 6,075,433 A | 6/2000 | Ono et al. |
| 4,968,437 A | 11/1990 | Noll et al. | | 6,097,293 A | 8/2000 | Galloway et al. |
| 4,971,687 A | 11/1990 | Anderson | | 6,118,249 A | 9/2000 | Brockmann et al. |
| 4,972,120 A | 11/1990 | Witting | | 6,150,986 A | 11/2000 | Sandberg et al. |
| 4,977,354 A | 12/1990 | Bergervoet et al. | | 6,160,371 A | 12/2000 | Tachikawa |
| 5,030,889 A | 7/1991 | El-Hamamsy et al. | | 6,161,032 A | 12/2000 | Acker |
| 5,039,903 A | 8/1991 | Farrall | | 6,166,494 A | 12/2000 | Green |
| 5,041,763 A | 8/1991 | Sullivan et al. | | 6,184,651 B1 | 2/2001 | Fernandez et al. |
| 5,047,715 A | 9/1991 | Morgenstern | | 6,188,179 B1 | 2/2001 | Boys et al. |
| 5,054,112 A | 10/1991 | Ike | | 6,194,828 B1 | 2/2001 | Kohne et al. |
| 5,070,293 A | 12/1991 | Ishii et al. | | 6,218,785 B1 | 4/2001 | Incerti |
| 5,101,332 A | 3/1992 | Hsia | | 6,241,359 B1 | 6/2001 | Lin |
| 5,115,168 A | 5/1992 | Shoda et al. | | 6,252,380 B1 | 6/2001 | Koenck |
| 5,122,729 A | 6/1992 | Itoga et al. | | 6,263,247 B1 | 7/2001 | Mueller et al. |
| 5,141,325 A | 8/1992 | Huang | | 6,275,143 B1 | 8/2001 | Stobbe |
| 5,146,140 A | 9/1992 | Piejak et al. | | 6,280,066 B1 | 8/2001 | Dolan |
| 5,158,361 A | 10/1992 | Huang | | 6,291,936 B1 | 9/2001 | MacLennan et al. |
| 5,184,891 A | 2/1993 | Shpigel | | 6,301,128 B1 | 10/2001 | Jang et al. |
| 5,216,402 A | 6/1993 | Carosa | | 6,307,316 B1 | 10/2001 | Holzer |
| 5,229,652 A | 7/1993 | Hough | | 6,322,226 B1 | 11/2001 | Dickson |
| 5,264,997 A | 11/1993 | Hutchisson et al. | | 6,326,739 B1 | 12/2001 | MacLennan et al. |
| 5,267,997 A | 12/1993 | Farin et al. | | 6,339,296 B1 | 1/2002 | Goral |
| 5,280,416 A | 1/1994 | Hartley et al. | | 6,345,203 B1 | 2/2002 | Mueller et al. |
| 5,281,941 A | 1/1994 | Bernstein | | 6,436,299 B1 | 8/2002 | Baarman et al. |
| 5,282,120 A | 1/1994 | Kijima | | 6,459,882 B1 | 10/2002 | Palermo et al. |
| 5,289,085 A | 2/1994 | Godyak et al. | | 6,462,432 B1 | 10/2002 | Seelig et al. |
| 5,300,860 A | 4/1994 | Godyak et al. | | 6,479,965 B2 | 11/2002 | Barbeau et al. |
| 5,301,096 A | 4/1994 | Klontz et al. | | 6,597,076 B2 | 7/2003 | Scheible et al. |
| 5,311,028 A | 5/1994 | Glavish | | 6,756,697 B2 | 6/2004 | Mizutani et al. |
| 5,339,233 A | 8/1994 | Yang | | 6,794,831 B2 | 9/2004 | Leeb et al. |
| 5,341,280 A | 8/1994 | Divan et al. | | 6,803,744 B1 | 10/2004 | Sabo |
| 5,367,242 A | 11/1994 | Hulman | | 6,924,767 B2 | 8/2005 | Kitahara et al. |
| 5,399,943 A | 3/1995 | Chandrasekaran | | 6,934,167 B2 | 8/2005 | Jang et al. |
| 5,416,388 A | 5/1995 | Shackle | | 7,164,255 B2 | 1/2007 | Hui |
| 5,422,519 A | 6/1995 | Russell | | 7,180,265 B2 | 2/2007 | Naskali et al. |
| 5,450,305 A | 9/1995 | Boys et al. | | 7,474,062 B2 | 1/2009 | Boys et al. |
| 5,455,466 A | 10/1995 | Parks et al. | | 7,479,742 B2 | 1/2009 | Matsui et al. |

| | | | |
|---|---|---|---|
| 2002/0008973 | A1 | 1/2002 | Boys et al. |
| 2002/0118004 | A1 | 8/2002 | Scheible et al. |
| 2002/0154518 | A1 | 10/2002 | Elferich et al. |
| 2003/0006880 | A1 | 1/2003 | Zimmer |
| 2003/0062980 | A1 | 4/2003 | Scheible et al. |
| 2003/0214821 | A1 | 11/2003 | Giannopoulos et al. |
| 2003/0222769 | A1 | 12/2003 | Mau |

FOREIGN PATENT DOCUMENTS

| | | |
|---|---|---|
| AT | 370929 | 5/1983 |
| AU | A-61741/86 | 2/1988 |
| DE | 2029468 | 12/1971 |
| DE | 2415087 | 10/1975 |
| DE | 2732950 | 2/1979 |
| DE | 3412237 | 10/1985 |
| DE | 4100272 | 7/1991 |
| DE | 9012505 | 8/1991 |
| DE | 4238688 | 5/1994 |
| DE | 4421253 | 3/1995 |
| DE | 4412957 | 10/1995 |
| DE | 19540854 | 5/1997 |
| EP | 0825577 | 2/1998 |
| EP | 1174082 | 1/2002 |
| FR | 2528656 | 12/1983 |
| FR | 2717614 | 9/1995 |
| GB | 778072 | 7/1957 |
| GB | 1349788 | 4/1974 |
| GB | 2204191 | 11/1988 |
| GB | 2326769 | 12/1998 |
| GB | 2388715 A | 11/2003 |
| GB | 2388716 A | 11/2003 |
| JP | 8-31585 | 2/1996 |
| JP | 2001327109 | 11/2001 |
| WO | WO 97/17761 | 5/1997 |
| WO | WO 97/26704 | 7/1997 |
| WO | WO 97/26705 | 7/1997 |
| WO | WO 00/22892 | 4/2000 |
| WO | WO 00/32298 | 6/2000 |
| WO | 0054387 | 9/2000 |
| WO | WO 00/54387 | 9/2000 |
| WO | WO 01/26427 | 4/2001 |
| WO | WO 01/26431 | 4/2001 |
| WO | 0167046 | 9/2001 |
| WO | WO 01/80396 A1 | 10/2001 |
| WO | 02/35578 | 5/2002 |
| WO | WO 03/096361 | 11/2003 |
| WO | WO 03/105311 | 12/2003 |

OTHER PUBLICATIONS

International Search Report, International Application No. PCT/US2004/001731, Sep. 9, 2004.

Written Opinion of the International Searching Authority, International Application No. PCT/US2004/001731, International Filing Date Jan. 22, 2004.

International Search Report, International Application No. PCT/US2004/001757, Sep. 24, 2004.

Written Opinion of the International Searching Authority, International Application No. PCT/US2004/001757, International Filing Date Jan. 22, 2004.

USPTO Office Action dated Sep. 21, 2005 for U.S. Appl. No. 10/689,224.

"A Contactless Electrical Energy Transmission System for Portable-Telephone Battery Chargers", IEEE Transactions on Industrial Electronics, vol. 50, No. 3, Jun. 2003.

"Best of Show", Fortune, Feb. 17, 2003.

"Splashpower", www.splashpower.com, Feb. 11, 2003.

"Mobilewise", www.mobilewise.com, Feb. 11, 2003.

Gulko, Michael, et al, Inductor-Controlled Current-Sourcing Resonant Inverter and its Application as a High Pressure Discharge Lamp Driver, IEEE, pp. 434-440, May 1994.

\* cited by examiner

*Primary Examiner* — David Hung Vu

(74) *Attorney, Agent, or Firm* — Warner Norcross & Judd LLP

(57) ABSTRACT

An inductive power supply system for providing power to one or more inductively powered devices. The system includes a mechanism for varying the physical distance or the respective orientation between the primary coil and secondary coil to control the amount of power supplied to the inductively powered device. In another aspect, the present invention is directed to an inductive power supply system having a primary coil and a receptacle disposed within the magnetic field generated by the primary coil. One or more inductively powered devices are placed randomly within the receptacle to receive power inductively from the primary coil. The power supply circuit includes circuitry for adjusting the power supplied to the primary coil to optimize operation based on the position and cumulative characteristics of the inductively powered device(s) disposed within the receptacle.

12 Claims, 27 Drawing Sheets

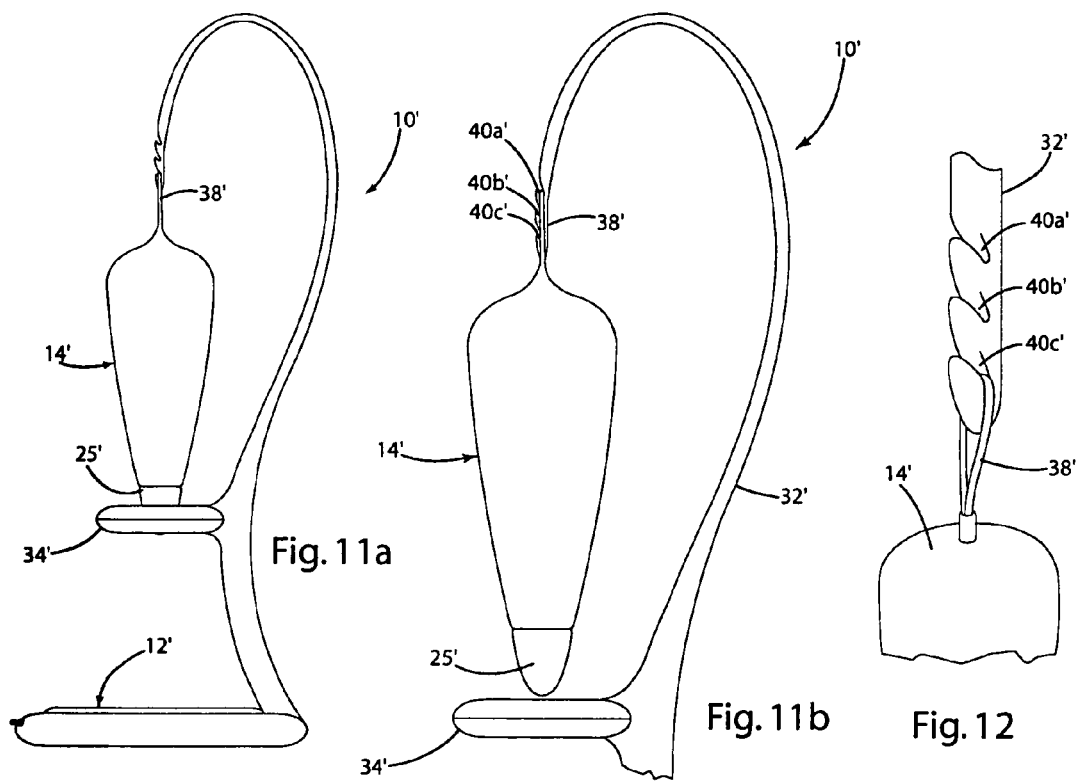

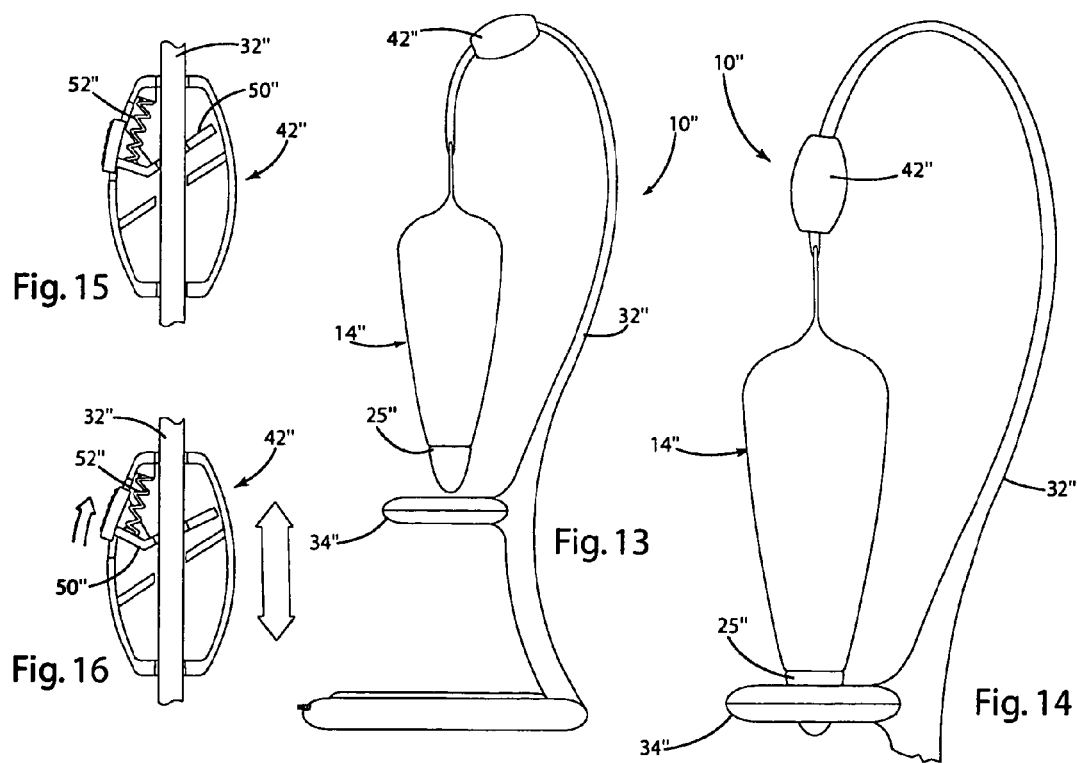

INDUCTIVELY POWERED APPARATUS

This is continuation of U.S. application Ser. No. 11/468, 149, which is a divisional of U.S. application Ser. No. 11/036, 688, filed Jan. 14, 2005 (now U.S. Pat. No. 7,233,222), which is a divisional of U.S. application Ser. No. 10/357,932, filed Feb. 4, 2003 (now U.S. Pat. No. 7,126,450), which is a continuation-in-part of U.S. application Ser. No. 10/133,860 entitled "Inductively Powered Lamp Assembly," which was filed on Apr. 26, 2002 (now U.S. Pat. No. 6,731,071), which is a continuation-in-part of U.S. application Ser. No. 09/592, 194 entitled "Fluid Treatment System," which was filed on Jun. 12, 2000 (now U.S. Pat. No. 6,436,299).

U.S. application Ser. No. 10/357,932 is also a continuation-in-part of U.S. application Ser. No. 10/246,155 entitled "Inductively Coupled Ballast Circuit," which was filed on Sep. 18, 2002 (now U.S. Pat. No. 6,825,620), which is a continuation-in-part of U.S. patent application Ser. No. 10/175,095 entitled "Fluid Treatment System," which was filed on Jun. 18, 2002 (now U.S. Pat. No. 6,673,250), which is a continuation-in-part of U.S. patent application Ser. No. 09/592,194 entitled "Fluid Treatment System," which was filed on Jun. 12, 2000 (now U.S. Pat. No. 6,436,299). U.S. patent application Ser. No. 09/592,194 (now U.S. Pat. No. 6,436,299) claims the benefit under 35 U.S.C. §119(e) of U.S. provisional patent application Ser. No. 60/140,159 entitled "Water Treatment System with an Inductively Coupled Ballast," which was filed on Jun. 21, 1999, and U.S. provisional patent application Ser. No. 60/140,090 entitled "Point-of-Use Water Treatment System," which was filed on Jun. 21, 1999.

U.S. application Ser. No. 10/357,932 is a continuation-in-part of U.S. application Ser. No. 29/165,043 entitled "Bulb," which was filed on Aug. 2, 2002 (now U.S. Pat. No D476, 095); U.S. application Ser. No. 29/165,008 entitled "Bowl Lamp," which was filed on Aug. 2, 2002 (now U.S. Pat. No. D479,356); U.S. application Ser. No. 29/165,012 entitled "Bulb," which was filed on Aug. 2, 2002 (now U.S. Pat. No. D476,094); U.S. application Ser. No. 29/165,005 entitled "Lamp," which was filed on Aug. 2, 2002 (now U.S. Pat. No. D479,892); U.S. application Ser. No. 29/165,009 entitled "Bulb," which was filed on Aug. 2, 2002 (now U.S. Pat. No. D475,471); and U.S. application Ser. No. 29/165,011 entitled "Chime," which was filed on Aug. 2, 2002 (now U.S. Pat. No. D478,834).

BACKGROUND OF THE INVENTION

The present invention relates to wireless power supplies, and more particularly to inductively powered devices.

The principles of inductive power transfer have been known for many years. As a result of mutual inductance, power is wirelessly transferred from a primary coil (or simply "primary") in a power supply circuit to a secondary coil (or simply "secondary") in a secondary circuit. The secondary circuit is electrically coupled with a device, such as a lamp, a motor, a battery charger or any other device powered by electricity. The wireless connection provides a number of advantages over conventional hardwired connections. A wireless connection can reduce the chance of shock and can provide a relatively high level of electrical isolation between the power supply circuit and the secondary circuit. Inductive couplings can also make it easier for a consumer to replace limited-life components. For example, in the context of lighting devices, an inductively powered lamp assembly can be easily replaced without the need to make direct electrical connections. This not only makes the process easier to perform, but also limits the risk of exposure to electric shock.

The use of inductive power transfer has, however, for the most part been limited to niche applications, such as for connections in wet environments. The limited use of inductive power transfer has been largely the result of power transfer efficiency concerns. To improve the efficiency of the inductive coupling, it is conventional to carefully design the configuration and layout of the primary and secondary coils. The primary and the secondary are conventionally disposed within closely mating components with minimal gap between the primary and the secondary. For example, the primary is often disposed within a base defining a central opening and the secondary is often disposed within a cylindrical component that fits closely within the central opening of the base. This and other conventional constructions are design to provide close coaxial and radial alignment between the primary coil and the secondary coil. Several specific examples of patents that reflect the conventional approach of providing a fixed, predetermined physical relationship between the primary and secondary coils include: U.S. Pat. No. 5,264,997 to Hutchisson et al, which discloses an inductive lamp with coaxial and closely interfitting primary and secondary coils; U.S. Pat. No. 5,536,979 to McEachern et al, which discloses an inductive charging device in which the device to be charged is fitted closely within a cradle to position the coils in a fixed, predetermined relationship; U.S. Pat. No. 5,949,155 to Tamura et al, which discloses a shaver with adjacent inductive coils set in a fixed relationship; U.S. Pat. No. 5,952,814 to Van Lerberghe, which discloses an inductive charger for a telephone wherein the physical relationship between the primary and secondary coils is fixed; and U.S. Pat. No. 6,028, 413 to Brockman, which discloses a charging device having a mechanical guide for ensuring precise, predetermined alignment between the inductive coils. The conventional practice of providing precise alignment between the primary and secondary coil has placed significant limitation on the overall design and adaptability of inductively powered devices. Further, in conventional inductive systems, the power supply circuit, which drives the primary coil, and the secondary circuit, which inductively receives power from the primary, are designed and carefully tuned to match with one another to maximize the efficiency of the inductive coupling. This too has placed significant limitations on the overall design and adaptability of inductively powered devices.

SUMMARY OF THE INVENTION

The aforementioned problems are overcome by the present invention wherein an inductively powered device is provided with a mechanism for varying the relative position between the primary and the secondary to control the amount of power supplied to the load. In one embodiment, the present invention is incorporated into a dimmable lamp assembly in which a primary is mounted to the lamp base and the secondary is mounted to the lamp assembly. The brightness of the lamp is controlled by adjusting the distance between the lamp assembly and the lamp base.

In a second embodiment, the present invention is incorporated into a dimmable lamp assembly in which the lamp brightness is controlled by varying the relative angular orientation of the primary and the secondary. In this embodiment, the primary is generally ring-shaped and the secondary is pivotally mounted within the ring. The lamp assembly includes a mechanical dimmer that rotates either the primary or the secondary so that their relative angular orientation varies. The variation in relative orientation varies the amount of power transferred to the secondary, thereby varying the brightness of the lamp.

In another embodiment, the present invention is incorporated into a wind chime having one or more lamps that vary in brightness based on the movement of the chimes. In this embodiment, a plurality of chime assemblies is suspended within a primary coil, with each chime assembly being individually movable. Each chime assembly includes a secondary disposed at its upper end within the magnetic field of the primary. As the wind blows, the chime assemblies swing with respect to the primary, thereby varying the locations and orientation of the secondary coils within the magnetic field of the primary. This causes the brightness of the wind chimes to vary in respond to the wind.

In yet another embodiment, the present invention provides an infinitely adjustable power supply for use with electrically powered devices where it is desirable to adjust the magnitude of power supplied to the device. The power supply includes an inductive coupling disposed between the power supply and the load. The inductive coupling includes a primary and a secondary. The infinitely adjustable power supply also includes an adjustment mechanism for selectively varying the relative position between the primary and the secondary, such as distance or angular orientation. The adjustment mechanism permits adjustment of the coupling coefficient and consequently the magnitude of power induced in the secondary and supplied to the load.

In a second aspect, the present invention is directed to an inductive power supply station that is capable of providing power to a plurality of inductive powered devices placed at random location and at random orientations with respect to the primary. The inductive power supply station generally includes a single primary arranged about a receptacle that is capable of receiving randomly placed inductively powered devices. The power supply circuit includes circuitry for adjusting the power supplied to the primary as a function of the inductively powered devices present in the receptacle. In one embodiment, the receptacle is a dish, bowl or similar structure in which one or more lamp assemblies can be placed to provide light. Each lamp assembly includes a secondary that inductively receives power from the primary. The brightness of the light can be controlled by varying the number of lamp assemblies placed in the receptacle and by moving the lamp assemblies within the receptacle.

In a third aspect, the present invention provides a secondary with a plurality of coils that are arranged at different orientations. The multiple coils permit the secondary to efficiently receive power when disposed at different orientations with respect to the primary. In one embodiment, a secondary with multiple coils is incorporated into an inductively powered lamp. The lamp assembly can receive maximum induced power when placed at different orientations within the magnetic field of the primary. In another embodiment, the lamp assembly includes a plurality of coils, each being electrically connected to a different light sources, for example, light sources of different colors. By adjusting the orientation of the lamp assembly, the color of emitted light can be varied by altering the respective brightness of the separate light sources.

These and other objects, advantages, and features of the invention will be readily understood and appreciated by reference to the detailed description of the preferred embodiment and the drawings.

BRIEF DESCRIPTION OF THE DRAWINGS

FIG. 11a is a side elevational view of an alternative desk lamp.

FIG. 11b is an enlarged side elevational view of a portion of the alternative desk lamp of FIG. 11a.

FIG. 12 is an enlarged perspective view of a portion of the alternative desk lamp of FIG. 11a showing the mechanical dimmer.

FIG. 13 is a side elevational view of a second alternative desk lamp.

FIG. 14 is an enlarged side elevational view of a portion of the second alternative desk lamp of FIG. 13.

FIG. 15 is a sectional view of a portion of the second alternative desk lamp of FIG. 13 showing the binding tab in the locked position.

FIG. 16 is a sectional view of a portion of the second alternative desk lamp of FIG. 13 showing the binding tab in the open position.

DETAILED DESCRIPTION OF THE PREFERRED EMBODIMENT

The present invention is directed to improvements in inductively powered devices. In a first aspect, the present invention provides a inductive coupling in which the relative position between the primary coil ("primary") and the secondary coil ("secondary") is selectively varied to permit control over the amount of power transferred to the secondary and consequently to the inductively powered device. This aspect of the invention is described in connection with various lamp configurations, for example, to permit control over the brightness of the light source. This aspect of the invention is also described in connection with other electrically powered devices where control over the amount of power supplied to the inductively powered device is desired. In a second aspect, the present invention is directed to an inductive power supply station. In this aspect, the present invention provides a receptacle for receiving one or more inductively powered devices at random locations and at random orientations. In one embodiment of this aspect, the secondary includes multiple coils arranged at different orientations so that power can be more efficiently induced in the secondary without precise alignment between the primary and secondary. In one embodiment, the secondary includes three coils oriented along the x, y and z axis of a Cartesian coordinate system so that power can be induced in the secondary regardless of the angular orientation of the secondary with respect to the primary.

Figure 1:
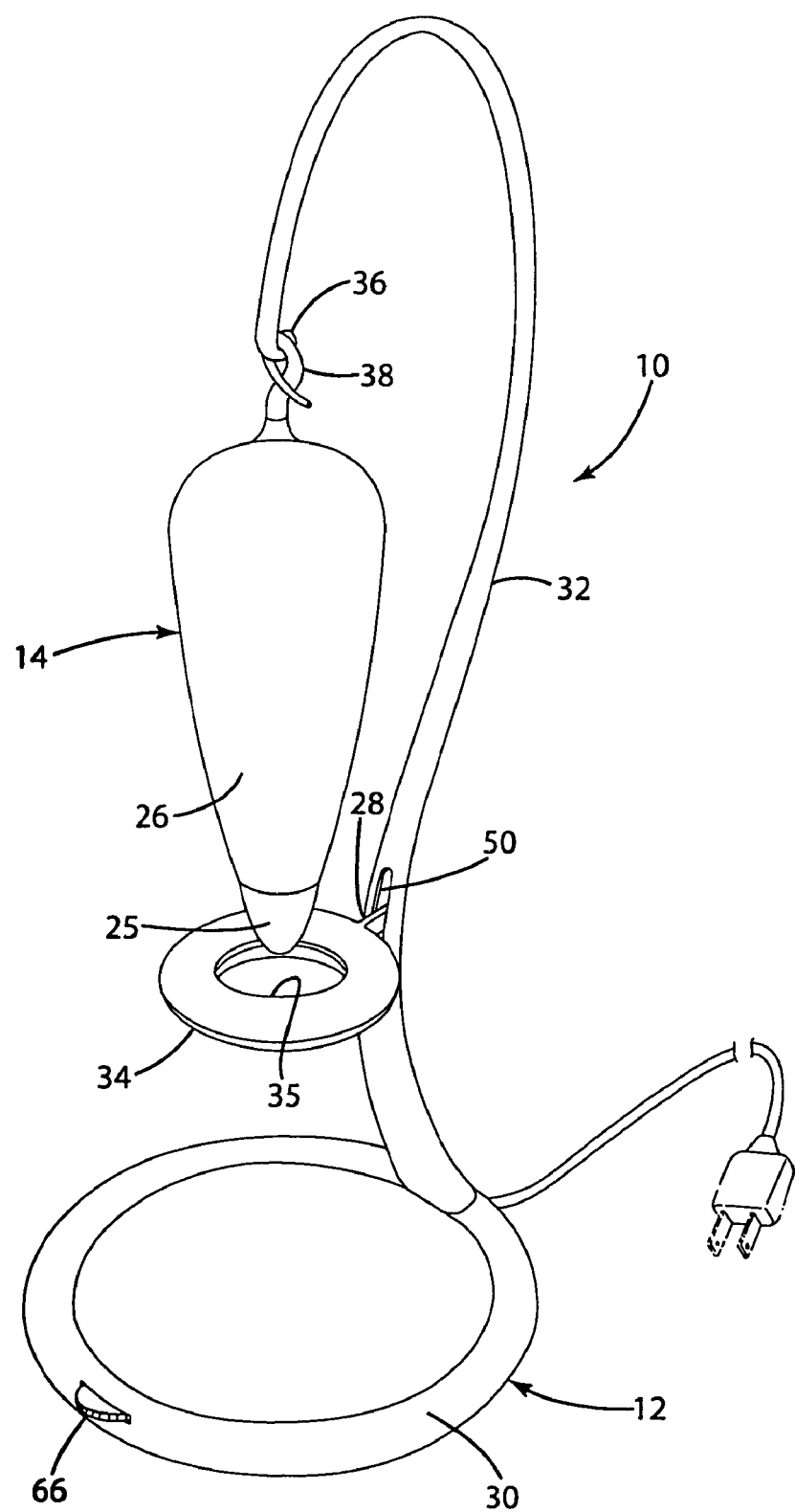
FIG. 1 is a perspective view of a desk lamp in accordance with an embodiment of the present invention.
Figure 2:
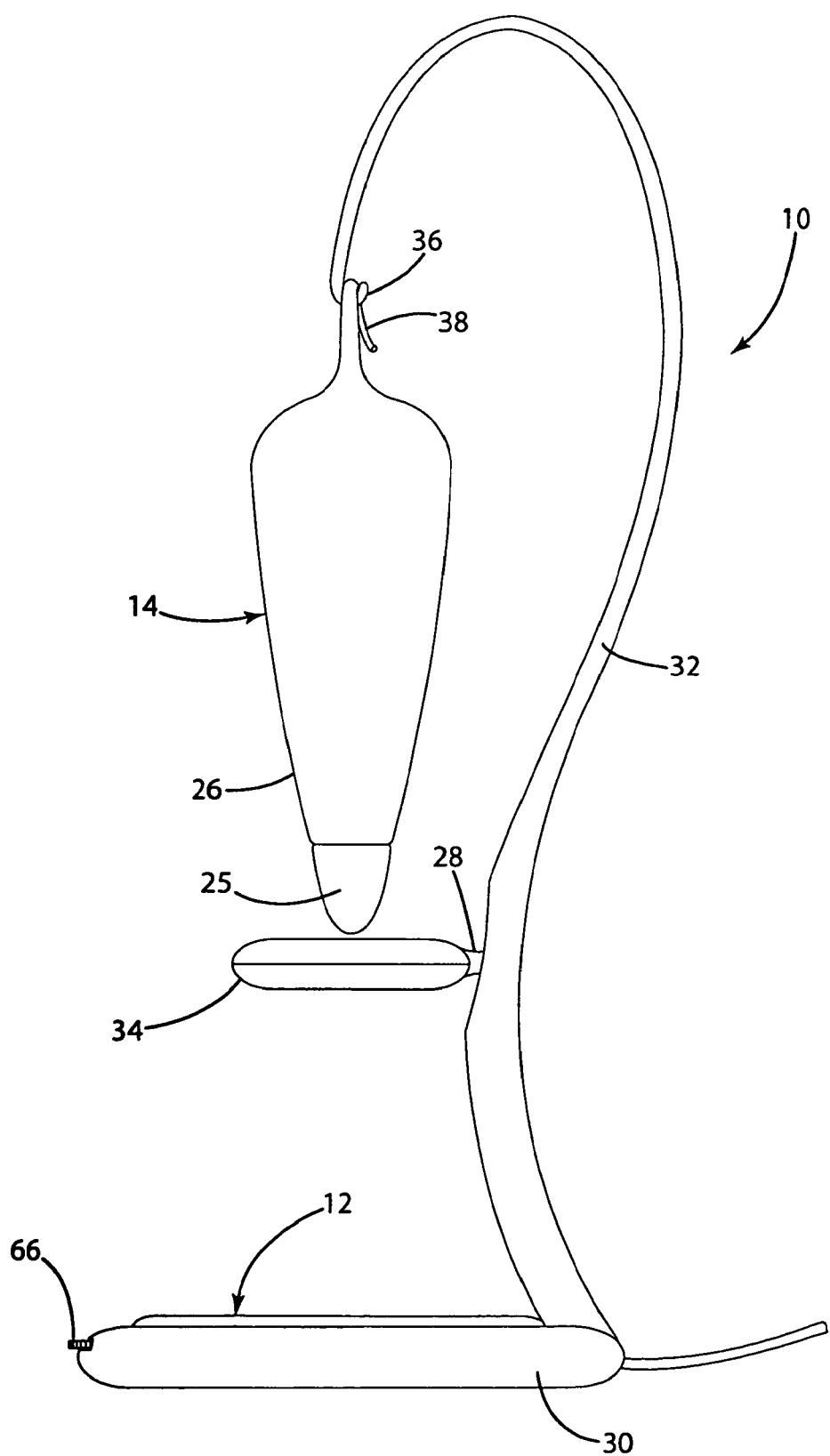
FIG. 2 is a side elevational of the desk lamp of FIG. 1.

An inductively powered desk lamp 10 in accordance with an embodiment of the present invention is shown in FIG. 1. The lamp 10 generally includes a base 12, a lamp assembly 14 and a mechanical dimmer 16 (See FIG. 3). The base 12 includes a ballast and power supply circuit 18 that drives a primary 20. The lamp assembly 14 includes a secondary circuit 22 having a secondary 24 that is inductively powered by the primary 20 and that applies power to the light source 26. The mechanical dimmer 16 includes a movable arm 28 that is movably attached to the lamp base 12. The primary 20 is mounted to the arm 28 so that movement of the arm 28 results in movement of the primary 20. The lamp assembly 14 is suspended from the lamp base 12 with the secondary 24 positioned within the electromagnetic field created by the primary 20. The arm 28 is mechanically movable to vary the position of the primary 20 with respect to the lamp assembly 14 (and consequently the secondary 24), thereby varying the coupling coefficient between the primary 20 and secondary 24. Changes in the coupling coefficient result in variation in the power transferred to the lamp assembly 14 and ultimately in the brightness of the light source 26. This aspect of the present invention is described in connection with a dimmable lamp 10. The present invention is, however, well-suited for use in virtually any application where variation in the amount of power transferred to the secondary circuit 20 is desired. For example, as described in more detail below, the present invention may be used to provide infinitely adjustable control over the amount of power supplied to a device up to the capacity of the power supply circuit.

Figure 3:
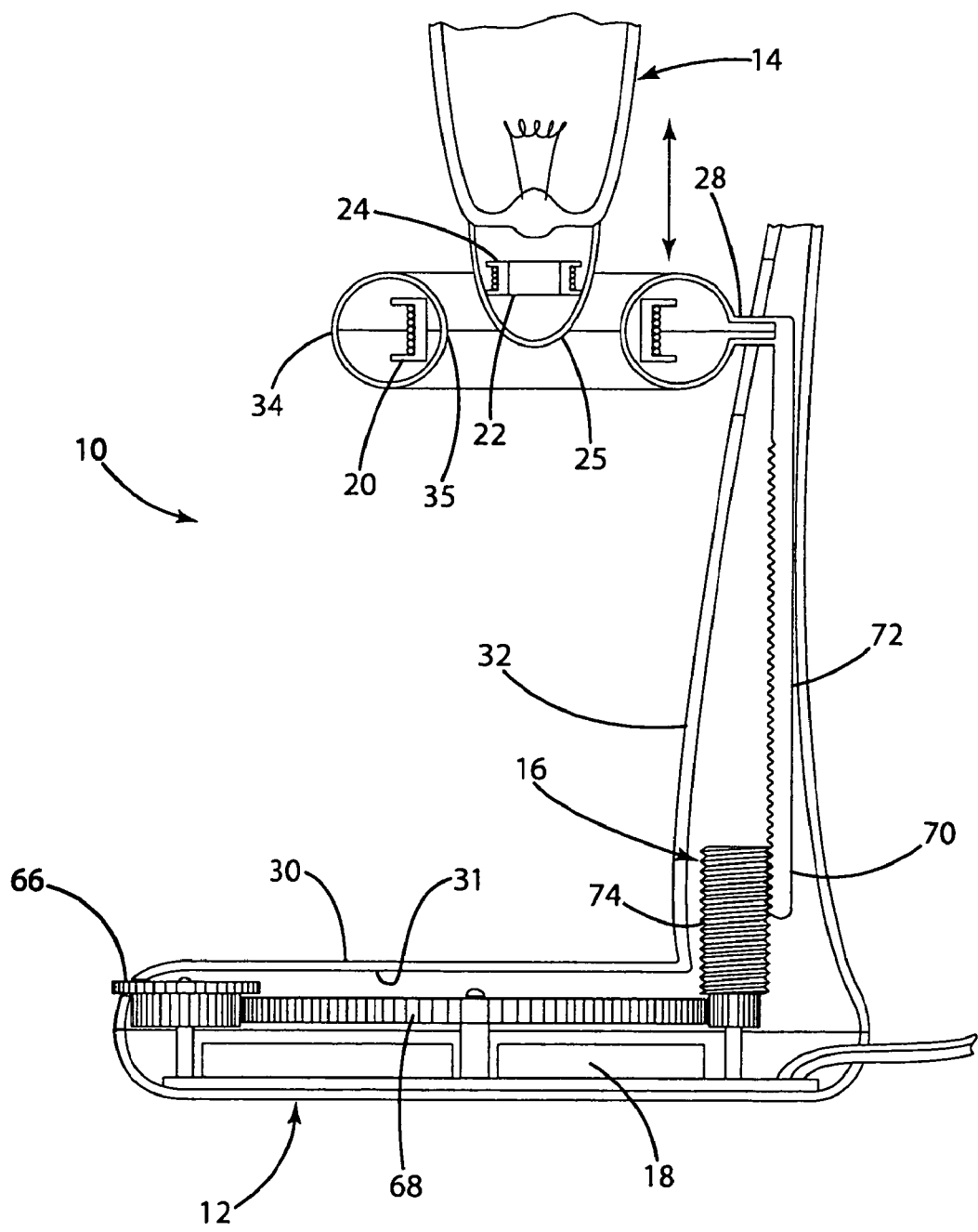
FIG. 3 is a partially sectional side elevational view of a portion of the desk lamp of FIG. 1.

As noted above, the desk lamp 10 of the illustrated embodiment generally includes a base 12, a lamp assembly 14 and a mechanical dimmer 16. The lamp base 12 generally includes a pedestal 30, a shaft 32 and a primary housing 34. The pedestal 20 of the illustrated embodiment is generally disc-shaped having a diameter of sufficient size to provide a stable support for the shaft 32 and lamp assembly 14, an internal void 31 adapted to house the power supply circuit 18 and portions of the mechanical dimmer 16. The shaft 32 extends upwardly from the pedestal to receive the lamp assembly 14. In the illustrated embodiment, the shaft 32 is somewhat "?"-shaped, providing an aesthetically pleasing visual appearance. The shaft 32 terminates at its upper end in a hook 36 or other connection element configured to receive the ring 38 of the lamp assembly 14. The primary housing 34 is generally ring-shaped and is hollow to provide a shell or housing for the primary 20. The primary housing 34 is mounted to the arm 28 to support the primary 20 in a position generally encircling the secondary housing 25 of the lamp assembly 14. The illustrated pedestal 30 and shaft 32 are provided with a desired aesthetic appearance. The present invention is easily adapted for use with lamps of a wide variety of designs. Accordingly, the design and configuration of the illustrated base 12 should not be interpreted as a limitation on the present invention. The power supply circuit 18 may be a conventional inductive power supply circuit, however, in one embodiment, the power supply circuit 18 includes a resonance seeking ballast, such as the ballast disclosed in U.S. application Ser. No. 10/246,155 entitled "Inductively Coupled Ballast Circuit," which was filed on Sep. 18, 2002, and is incorporated herein by reference. In the illustrated embodiment, the principle components of the power supply circuit 18 are housed within the void 31 in pedestal 30, for example, as shown in FIG. 3. The location of the components of the power supply circuit 18 may, however, vary from application to application depending primarily on the lamp design and desired aesthetics. For example, the principle components of the power supply circuit 18 can alternatively be disposed at other locations in or on the pedestal 30 or may be disposed in or on the shaft 32. As a further alternative, some or all of the components of the power supply circuit 18 can be integrated into a wall plug (not shown) for the lamp 10. In the illustrated embodiment, the primary 20 is generally ring-shaped and is mounted within a generally ring-shaped primary housing 34. The primary housing 34 defines a central opening 35 that is of sufficient dimension to receive at least a portion of the lamp assembly 14. The size, shape and orientation of the primary 20 (and primary housing 34) can vary from application to application depending in part on the specific design characteristics of the lamp or other inductive device. In the described embodiment, the primary 20 has an inner diameter of 1.25 inches and includes 50 turns of wire 63 wrapped circumferentially around a generally conventional plastic bobbin 33. The wire 63 may be straight 26-gauge wire. Additionally, in this particular embodiment, the values of capacitors 271 and 272 in the above-referenced patent application are 66$n$F.

Figures 4, 5:
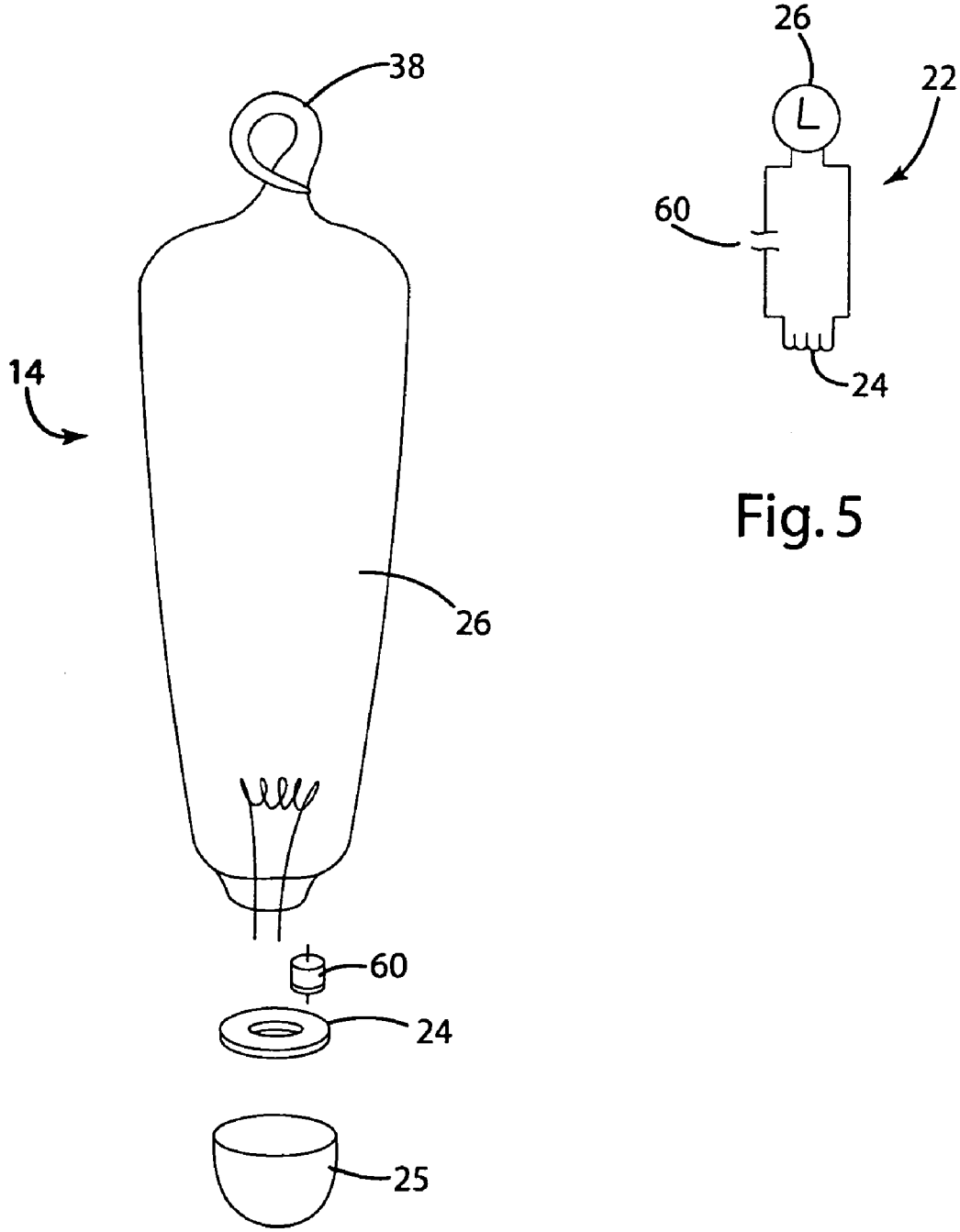
FIG. 4 is an exploded view of a lamp assembly in accordance with one embodiment of the present invention.
FIG. 5 is a schematic of a secondary circuit.

The lamp assembly 14 generally includes a light source 26, such as an incandescent bulb, that is powered by a secondary circuit 22 (See FIGS. 4 and 5). In this embodiment, the light source 26 is custom formed to provide the desired aesthetic appearance. The upper end of the light source 26 is shaped to define a small ring 28 that permits the light source 26 to be hung from a hook 36 defined at the end of shaft 32. The custom-formed lamp of the illustrated embodiment is merely exemplary, and the light source 26 may vary from application to application as desired. As an alternative to the custom-formed lamp 26, the lamp assembly 14 may include a conventional lamp (not shown) that is contained within a housing (not shown) designed to provide the desired aesthetic appearance. For example, the custom-shaped light source 26 can be replaced by a standard incandescent light source that is installed within an ornate and aesthetically pleasing housing. In this alternative embodiment, the secondary circuit 22 may also be enclosed within the housing.

As noted above, the lamp assembly 14 includes a secondary circuit 22 that provides power to the lamp 26. The secondary circuit 22 includes a secondary 24 that is inductively driven by the primary 20. A schematic diagram of the secondary circuit is shown in FIG. 5. In this embodiment, the light source 26 is a custom-formed incandescent 30-watt bulb. The light source 26 is electrically connected in series with the secondary 24 and, if desired, a capacitor 60. In this embodiment, the secondary 24 has a diameter of 0.25 inches and includes 24 turns of wire 64 wrapped circumferentially around a generally conventional plastic bobbin 62. The wire 64 may be straight. 26-gauge wire. The optional capacitor 60 is intended to improve the power factor of the secondary circuit 22 by offsetting the inductance of the secondary 24, as described in more detail in U.S. application Ser. No. 10/133,860 entitled "Inductively Powered Lamp Assembly," which was filed on Apr. 26, 2002 and is incorporated herein by reference. In this embodiment, the capacitor 60 includes a capacitance of 33$n$F. The characteristics of the secondary circuit 22, including the secondary 24 and the capacitor 60, may vary from application to application depending primarily on the characteristics of the light source and the power supply. In fact, as noted above, the capacitor 60 is optional and may be eliminated altogether in some applications. Although this embodiment includes an incandescent light source 26, the present invention can alternatively include essentially any other electromagnetic radiation emitting device, such as a gas discharge bulb or a light emitting diode.

Figure 6:
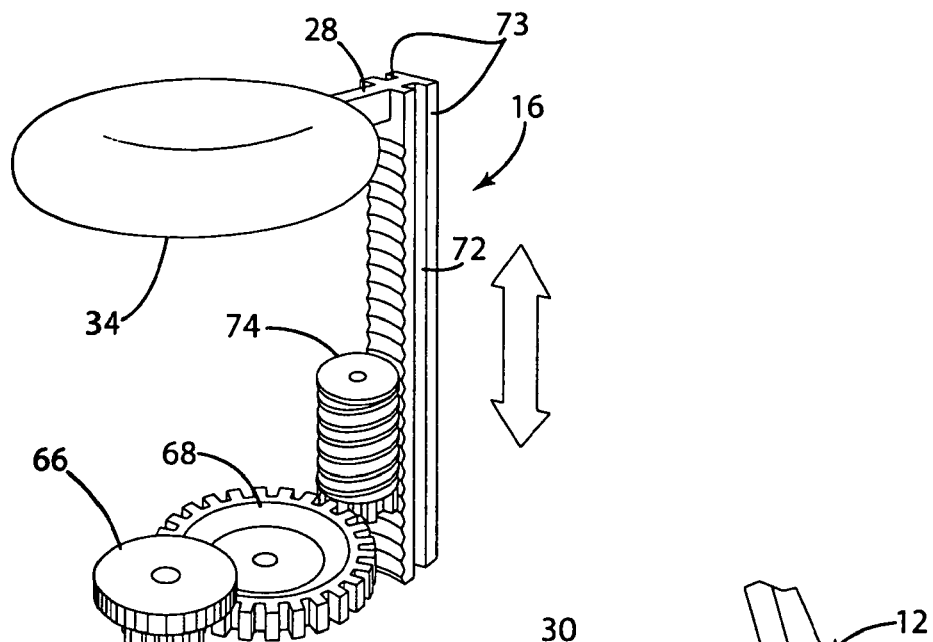
FIG. 6 is a perspective view of a rack-and-worm mechanical dimmer.
Figure 7:
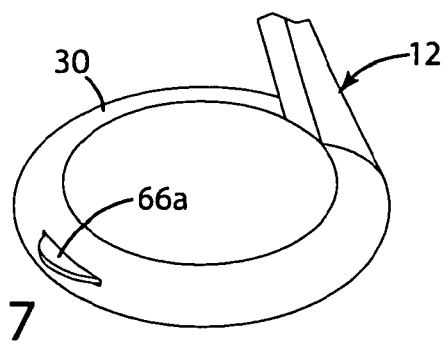
FIG. 7 is a perspective view of the base of a desk lamp showing a dial.
Figure 8:
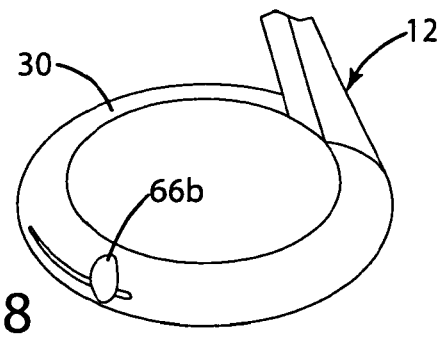
FIG. 8 is a perspective view of the base of a desk lamp showing a slider.
Figure 9:
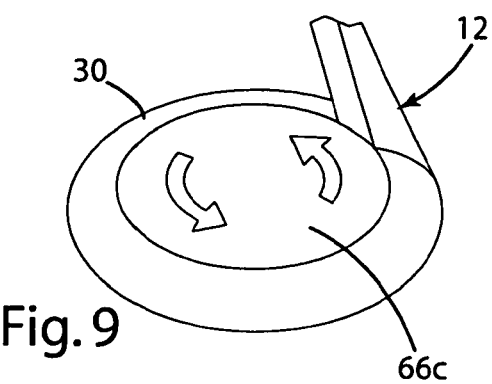
FIG. 9 is a perspective view of the base of a desk lamp showing a rotating top.

As described above, the desk lamp 10 is provided with a mechanical dimmer 16 for controlling the brightness of the light source 26. In the illustrated embodiment, the mechanical dimmer 16 is incorporated into the base 12 and shaft 32 to provide vertical movement of the primary housing 34 (and consequently the primary 20) and vary the physical distance between the primary 20 and the secondary 24. As shown, the primary housing 34 is mounted on movable arm 28. In this embodiment, the arm 28 extends through a vertical slot 50 in the shaft 32 and is connected to the rack 72 of a rack-and-worm assembly 70. In this embodiment, the lamp base 12 may include a dial 66$a$ (See FIG. 7), a slider 66$b$ (See FIG. 8) or a rotating top 66$c$ (See FIG. 9) for controlling movement of the mechanical dimmer 16. The rack-and-worm assembly 70 translates rotational movement of the dial 66$a$, slider 66$b$ or rotating top 66$c$ into vertical movement of the primary 20 in accordance with conventional mechanical principles. More specifically, movement of dial 66$a$, slider 66$b$ or rotating top 66$c$ causes rotation of worm gear 74, which is rotatably fixed within the lamp base 12 or shaft 32. In the illustrated embodiment, dial 66$a$ is connected to worm gear 74 by spur gear 68. As a result, rotational movement of dial 66$a$ causes rotational movement of spur gear 68 and ultimately worm gear 74. Movement of worm gear 74 in turn causes vertical linear movement of the rack 72 and consequently the primary 20. As perhaps best shown in FIG. 6, the rack 72 includes longitudinal slots 73 that are interfitted with corresponding ribs (not shown) on the interior of the shaft 32. This interface permits vertical movement of the rack 72 within the shaft 32. Because of the non-reversible nature of a worm gear assembly (i.e. the worm 74 can move the rack 72, but the rack 72 cannot rotate the worm gear 74), it provides a "self-locking" mechanical dimmer 16. The electrical leads (not shown) running from the power supply circuit 18 to the primary housing 34 are provided with sufficient slack to permit the desired range of motion. Alternatively, sliding contacts (not shown) can be provided to maintain an electrical connection between the power supply circuit 18 and the primary 20 throughout the entire range of motion of the mechanical dimmer 16.

Figure 10:
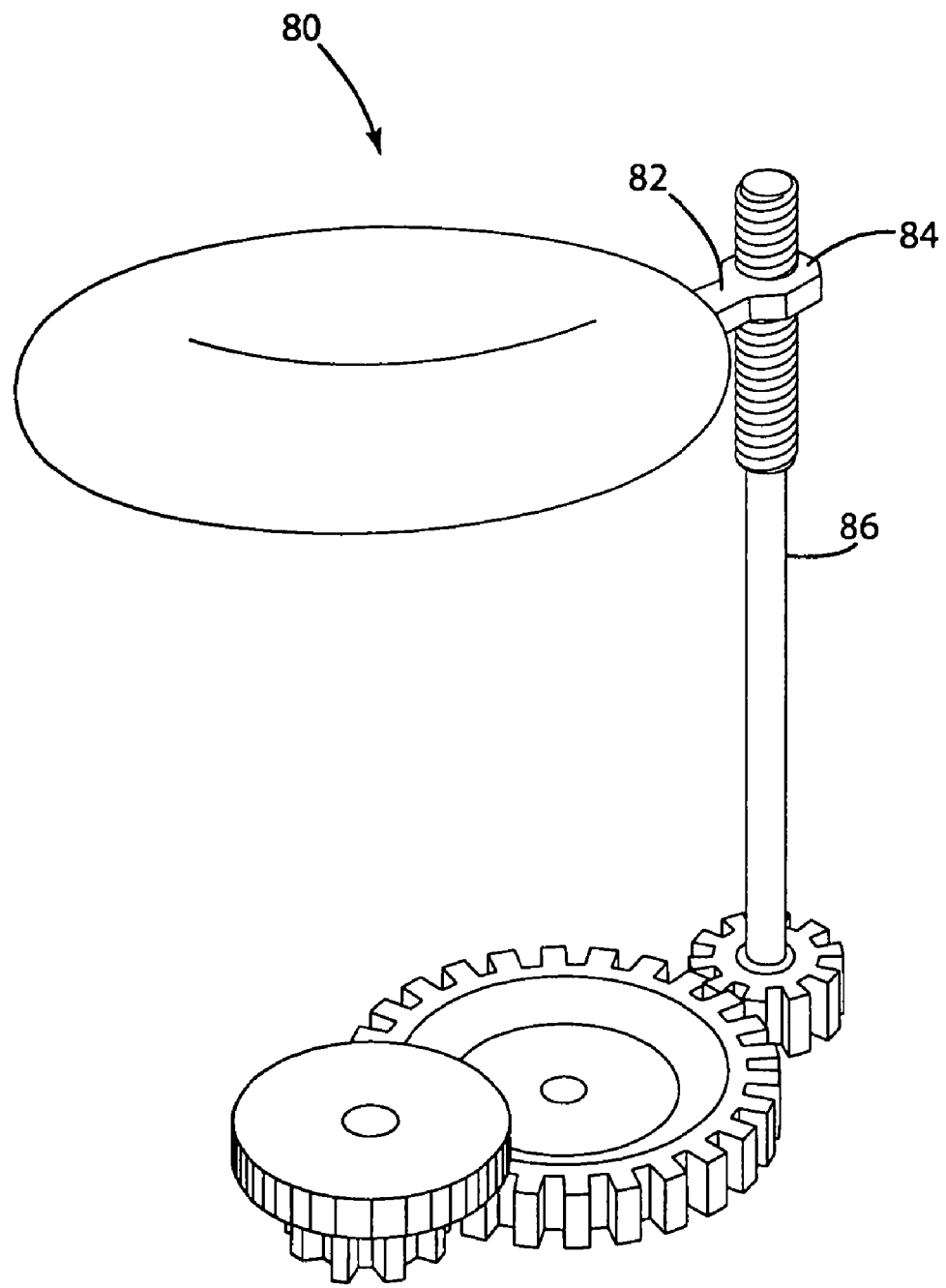
FIG. 10 is a perspective view of an alternative mechanical dimmer.
Figure 17:
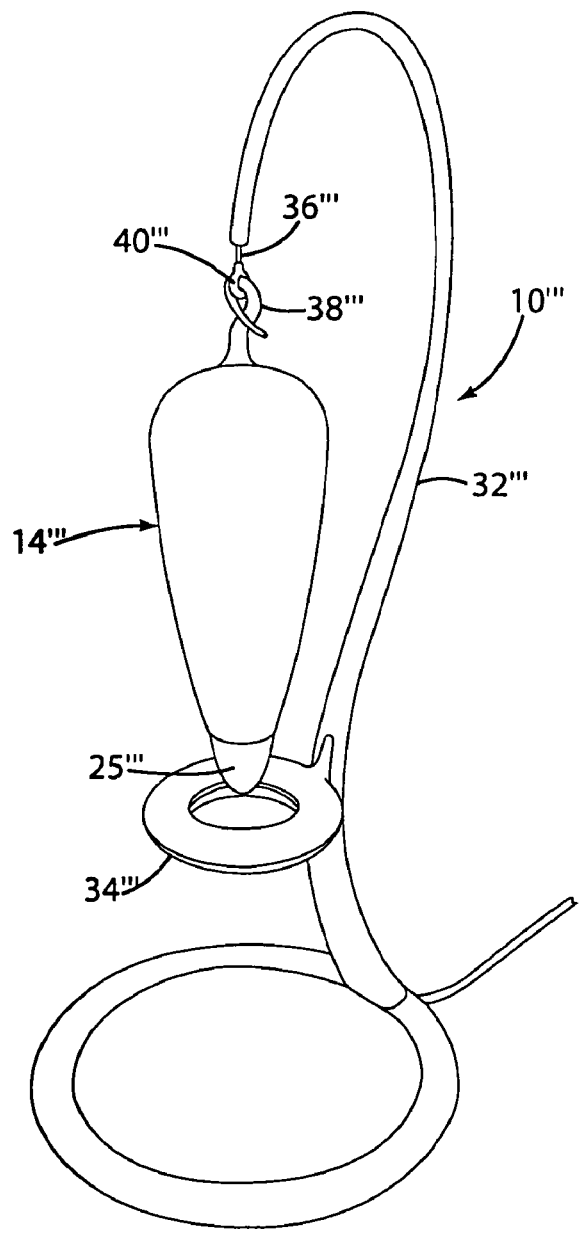
FIG. 17 is a perspective view of a third alternative desk lamp.

An alternative mechanical dimmer 80 is shown in FIG. 10. In this alternative embodiment, the inner end of the arm 82 includes a nut 84 that is movable mounted over a threaded rod 86. The height of the arm 82 is adjusted by rotating the threaded rod 86, which causes the nut 84 to move up and down the shaft of the rod 86. The rod 86 may be rotated using essentially any type of control, such as dial 66$a$, slider 66$b$ or rotating top 66$c$. As with the rack-and-worm embodiment described above, slack electrical leads, sliding contacts or other similar mechanisms can be provided to maintain electrical connection throughout the desired range of motion of the arm 82.

Figure 18:
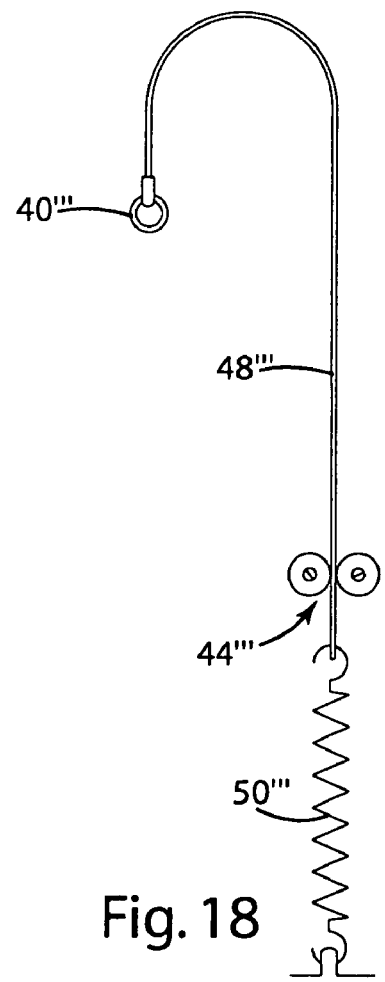
FIG. 18 is a perspective view of the mechanical dimmer of the third alternative desk lamp of FIG. 17.
Figure 19:
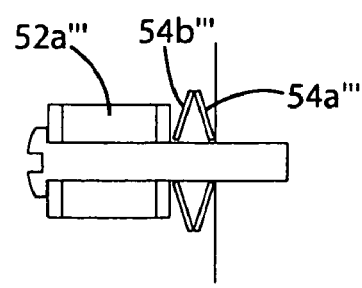
FIG. 19 is a sectional view of a portion of the mechanical dimmer of the third embodiment.

The mechanical dimmer may alternatively be configured to provide movement of the lamp assembly 14 with respect to the primary 20. This alternative may be preferable in some applications because it may simplify the electrical configuration of the system. More specifically, because there is no relative movement between the power supply circuit 18 and the primary 20, wires or other electrical connections can be run directly from the power supply circuit 18 to the primary 20 without any accommodation for relative movement (e.g. slack electrical leads or sliding contacts). Further, because the lamp assembly 14 is self contained, there is no need to run electrical connections to the lamp assembly 14. In one embodiment of the desk lamp 10' manufactured in accordance with this alternative, the shaft 32' includes a plurality of notches 40$a$-$c$' capable of receiving the lamp assembly 14' (See FIGS. 11$a$-$b$ and 12). In this embodiment, the upper end of the lamp assembly 14' is provided with an enlarged ring 38' capable of being fitted into the notches 40$a$-$c$'. As illustrated, the lamp assembly 14' can be suspended from different notches 40$a$-$c$' to vary the position of the secondary housing 25' with respect to the primary housing 34'. This in turn varies the brightness of the lamp assembly 14'. In a second embodiment of an alternative desk lamp 10", the shaft 32" is manufactured from a flexible material that is capable of bending to vary the position of the lamp assembly 14" with respect to the primary housing 34", and consequently the position of the secondary with respect to the primary. In some applications, the flexible shaft 32" may have little or no resiliency so that it remains in whatever position it is bent into under acted on. In other applications, the flexible shaft 32" may be resilient so that a mechanism is required to hold the shaft 32" in the desired position. In one embodiment of this type of application shown in FIGS. 13-16, a weight 42" is fitted over and movable along the shaft 32" to set and maintain the shaft 32" at the desired bend (See FIGS. 13 and 16). In one embodiment, the weight 42" is fitted over the shaft 32" and includes a generally conventional, spring-loaded binding clip 50" that selectively locks the weight in place on the shaft 32". In operation, spring 52" biases the binding clip 50" into a binding position on the shaft 32". To move the weight, the binding clip 50" is pushed against the bias of spring 52" into a released position in which the binding clip 50" is free to slide along the shaft 32". In a third embodiment of the desk lamp 10''', a counterbalance assembly 44''' is used to set the position of the lamp assembly 14'''. In this embodiment, the shaft 32''' is preferably hollow, defining an internal space (not shown) to contain the counterbalance assembly 44'''. The lamp assembly 14''' is suspended from the shaft 32''' by a cable 48'''. The cable 48''' extends through the internal space in the shaft 32''' and is fixed to the counterbalance assembly 44'''. A ring 40''' is mounted to the free end of the cable 48''' to interconnect with the lamp assembly ring 38'''. As best shown in FIG. 18, the counterbalance assembly 44 generally includes a spring 50''' (or other biasing mechanism) with a tension that offsets the weight of the lamp assembly 14'''. The counterbalance assembly 44 also includes a pair of rollers 52a-b''' that firmly entrap the cable 48'''. The rollers 52a-b''' are fitted with Bellville washers 54a-b''' to provide a limiting brake that retains the cable 48''' in a given position (See FIG. 19). By offsetting the weight of the lamp assembly 14", the counterbalance assembly 44 holds the lamp assembly 14''' in the position selected by the user. This allows the user to set the brightness of the lamp assembly 14''' simply by raising or lowering the lamp assembly 14'''. Alternatively, the spring 50''' can be replaced by a counterbalance weight (not shown) having approximately the same weight as the lamp assembly 14'''.

In a further alternative embodiment (not shown), the mechanical dimmer may include a mechanism for moving the secondary within the lamp assembly rather than moving the entire lamp assembly. For example, the lamp assembly may include a secondary that is slidably movably mounted along a fixed shaft so that the user can slide the secondary up or down the shaft to control the brightness of the lamp assembly (not shown). Alternatively, the secondary may be rotatably mounted within the secondary housing to permit changes to the angular orientation of the secondary, for example, by mounting the secondary on a ball joint (not shown). Knobs or handles (not shown) may protrude through slots in the secondary housing to facilitate the linear or angular movement. The mechanical dimmer may alternatively include a similar mechanism (not shown) for moving the primary within the primary housing.

Figure 20:
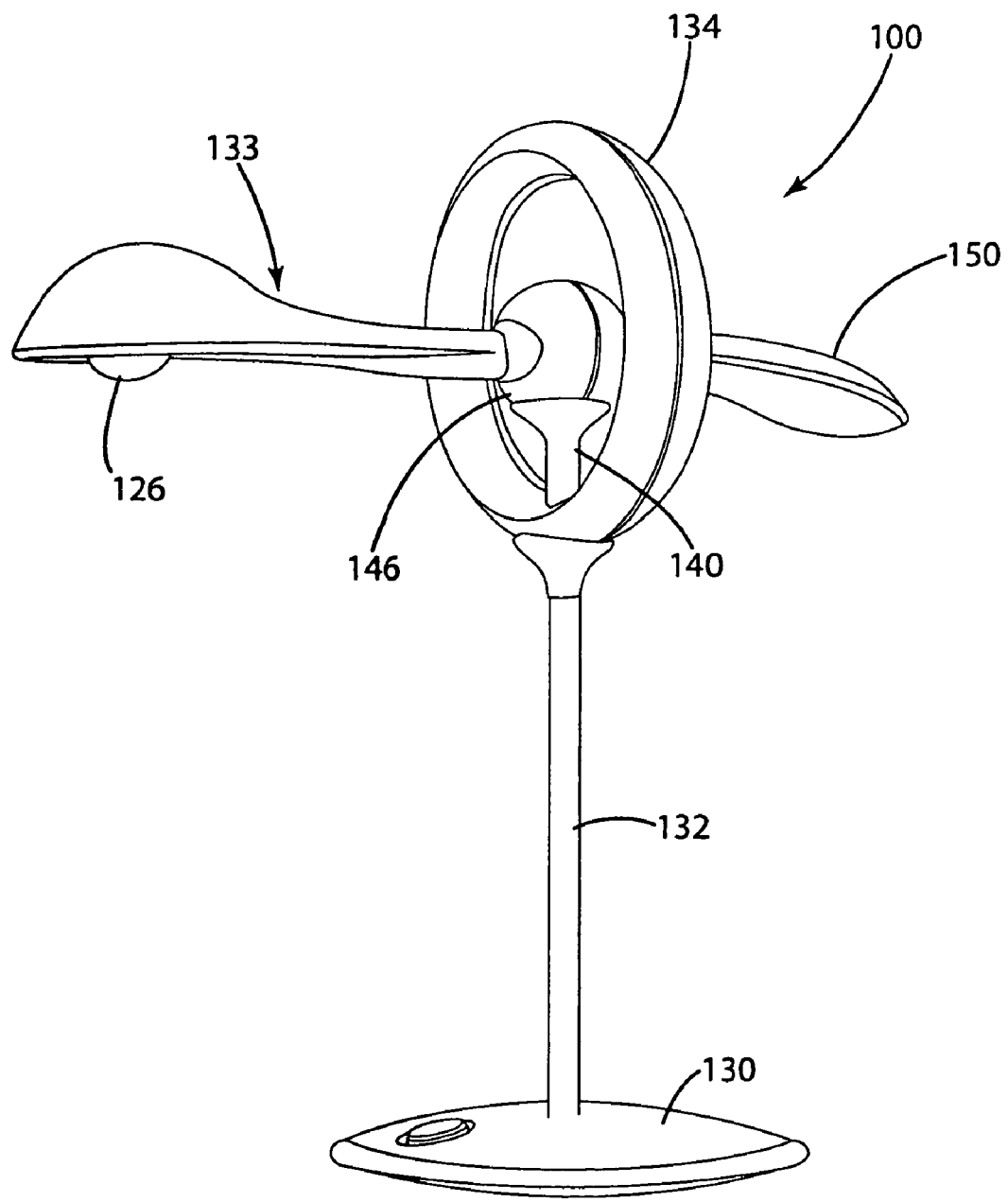
FIG. 20 is a perspective view of a fourth alternative desk lamp.
Figure 22:
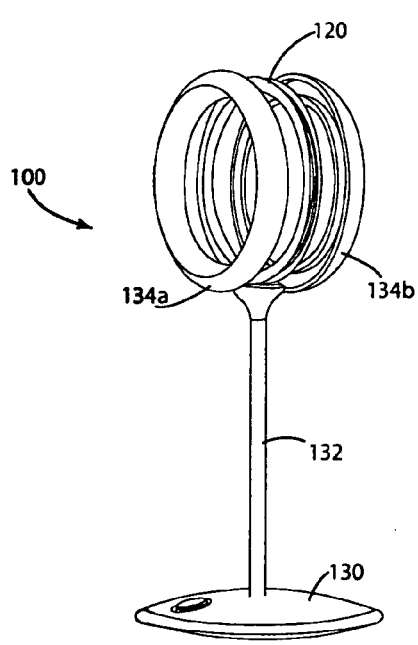
FIG. 22 is a partially exploded perspective view of the third alternative desk lamp with portions removed to show the primary housing.
Figure 21:
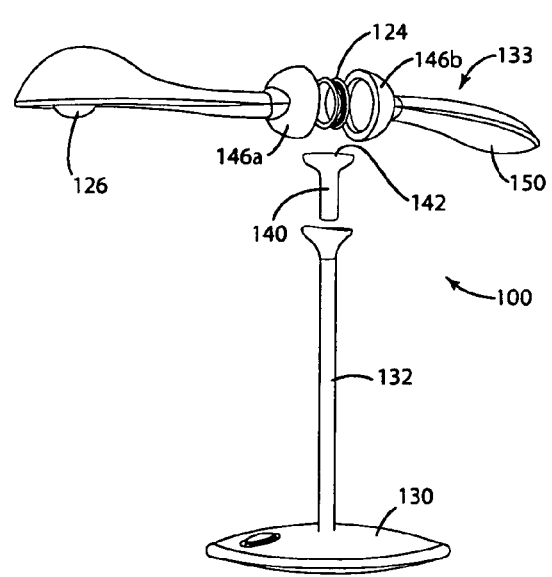
FIG. 21 is a partially exploded perspective view of the third alternative desk lamp with portions removed to show the arm.

An alternative inductively powered lamp 100 is shown in FIGS. 20-22. In this embodiment, the amount of power supplied to the secondary component is controlled by varying the relative angular orientation of the secondary 124 with respect to the primary 120. The lamp 110 generally includes a pedestal 130, a shaft 132 mounted to the pedestal 130 and an arm 133 pivotally mounted to the shaft 132. In one embodiment, light source 126 is located toward one end of arm 133, and a counterbalance 150 is located toward the opposite end. The power supply circuit is preferably contained primarily in the pedestal 130 and the shaft 132, and includes a primary 120 that is mounted toward the top of the shaft 132 in a ring-shaped primary housing 134. The primary housing 134 may be assembled from injection molded halves 134a-b. A support 140 extends upwardly from the shaft 132 into the central opening defined by the primary housing 134. The support 140 defines a concave cradle 142 adapted to receive the arm 133. The arm 133 includes a sphere 146 disposed at the center of gravity of the arm 133. The sphere 146 may be assembled from injection molded halves 146a and 146b, and includes an outer diameter that corresponds with the inner diameter of the cradle 142. Accordingly, the arm 133 is mounted to the shaft 132 by resting it upon the support 140 with sphere 146 received in cradle 142. If desired, the stability of the arm 133 may be improved by heavily weighting the sphere 146. The illustrated connection permits pivotal movement of the arm 133 in essentially all directions. A variety of alternative joints can be used to connect the arm 133 to the shaft 132. For example, a standard ball and socket or a standard universal joint can replace the illustrated connection. If desired, a connection providing only limited movement of the arm 133, such as only vertical or only horizontal movement, may be used.

In operation, the arm 133 is pivotally moved with respect to the shaft 132 causing a rolling action of sphere 146 within cradle 142. As the arm 133 is moved, the secondary 124 pivots within the magnetic field generated by the primary 120. This varies the coupling coefficient and the brightness of the light source 126. The secondary 124 and primary 120 can be oriented to provide the brightest light at the desired position of the arm 133. For example, the light source 126 may be its brightest when the arm 133 is substantially horizontal and increasingly dim as the arm 133 is moved up or down out of the horizontal position. Alternatively, the light source 126 may become brighter as the arm 133 is moved downward below horizontal. Counterbalance 150 is provided to counter the weight of light source 126, thereby maintaining the relative position of arm 133 unless acted upon.

The previously described embodiments are directed to lighting applications in which the brightness of the light source is controlled by mechanisms that vary the relative position of primary and secondary. The present invention is not, however, limited to lighting application. Rather, the present invention is well suited for use in essentially any application when control over the amount of power supplied to a device is desired. In this aspect, the present invention provides an infinitely adjustable inductive power supply. By providing a mechanism for controlling the position of the secondary with respect to the primary, the amount of power supplied through the inductive coupling can be controlled. More specifically, by adjusting the distance between the primary and the secondary or the angular orientation between the primary and the secondary, the coupling coefficient of the inductive coupling can be infinitely adjusted within the range of the inductive power supply. In this aspect, the present invention not only provides an infinitely adjustable power source, but it also provides isolation between the power supply and the inductively powered device, thereby providing safety benefits.

Figure 23:
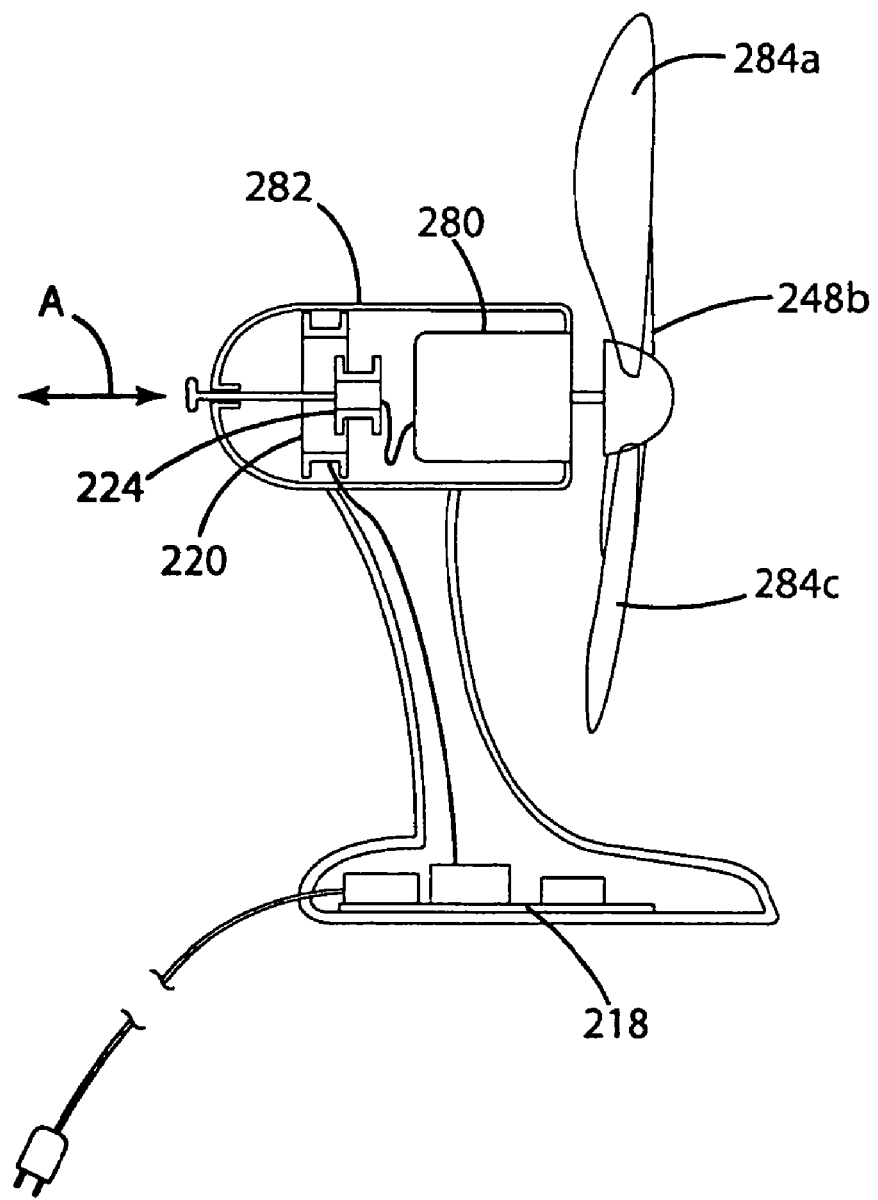
FIG. 23 is a partially sectional side elevational view of a variable speed fan incorporating an infinitely adjustable power supply in accordance with an embodiment of the present invention.

An adjustable power supply in accordance with the present invention is described in more detail in connection with the variable speed fan 200 shown in FIG. 23. In the illustrated embodiment, the fan 200 includes a conventional electric motor 280 that is housing within a generally conventional fan housing 282. The fan 200 includes a plurality of fan blades 284a-c that are mounted to the rotor (not shown) of the electric motor 280. The electric motor 280 receives power from a power supply circuit 218 having a primary 220 and a secondary 224. The secondary 224 is movably mounted adjacent to the primary 220 so that movement of the secondary 224 can be used to selectively vary the coupling coefficient of the inductive coupling and, in turn, vary the power supplied to the motor 280. For example, in the illustrated embodiment, the secondary 224 is mounted to adjustment rod 290. The adjustment rod 290 is movable inwardly and outwardly with respect to the fan housing, as indicated by arrow A, to move the secondary 224 with respect to the primary 220. As a result, adjustment of the secondary 224 can be used to selectively control the speed of the fan 200. Although this embodiment includes a mechanism for moving the secondary 224, the coupling coefficient can alternatively be adjusted by providing a mechanism for moving the primary 220 or for moving both the primary 220 and the secondary 224. As noted above, adjustment of the coupling coefficient can be achieved by varying the physical distance between the primary and the secondary and/or by varying the relative angular orientation between the primary and the secondary.

Figure 24:
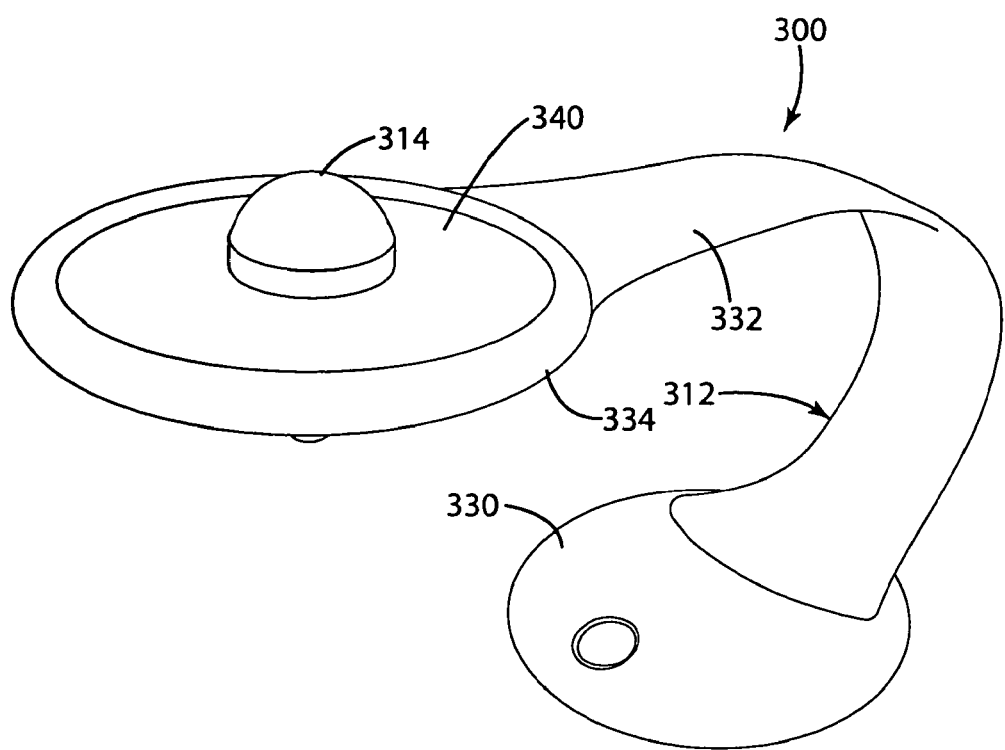
FIG. 24 is a perspective view of a fifth alternative desk lamp.
Figure 25:
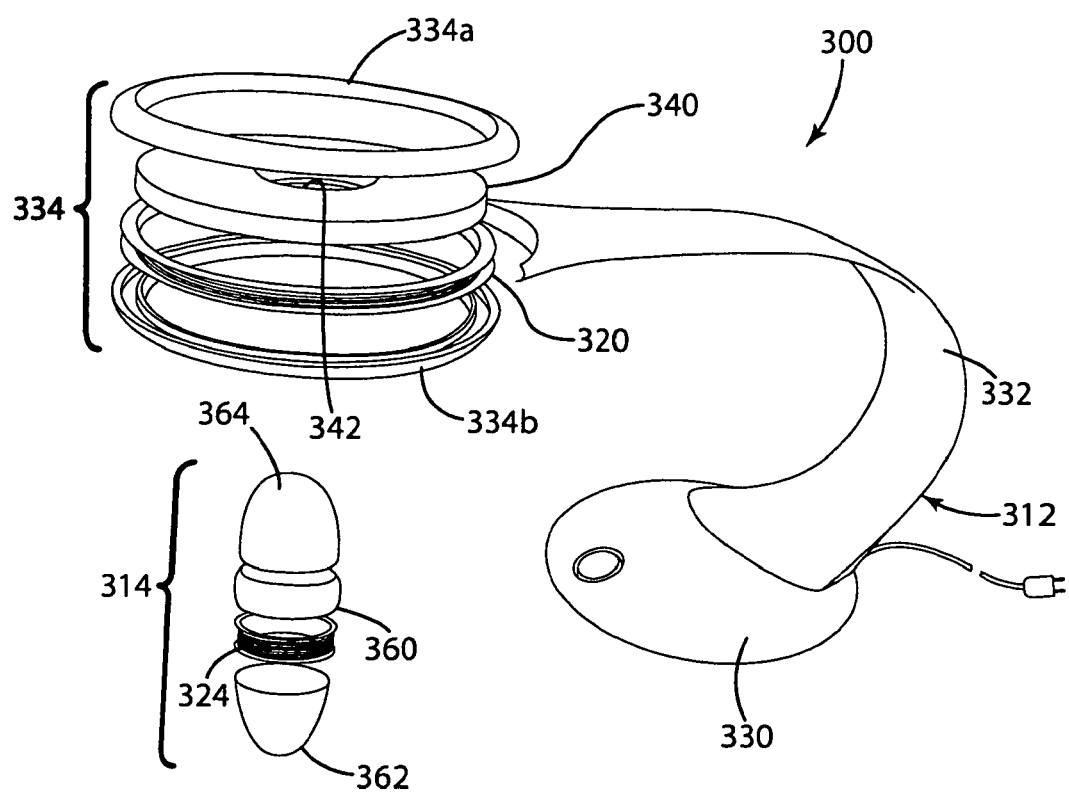
FIG. 25 is a partially exploded perspective view of the fifth alternative desk lamp of FIG. 24.

Although described in connection with a variable speed fan, the infinitely adjustable power supply of the present invention is well suited for use in other applications where an adjustable power supply is desired. For example, the power supply may be incorporated into a battery charger (not shown), where the magnitude of the charging power is controlled by adjusting the relative position of the primary and the secondary. As a further example, the power supply may be incorporated into an electric drill (not shown) or other electric power tool, where the power supplied to the electric motor is adjusted by selectively varying the relative position between the primary and the secondary In another embodiment, a desk lamp 300 is provided with a lamp assembly 314 that can be positioned in different orientations to vary the characteristics of the light output. In the embodiment illustrated in FIGS. 24 and 25, the desk lamp 300 includes a lamp assembly 314 that can be positioned in either an upright or inverted position with the two positions creating different lighting effects. As shown, the desk lamp 300 includes a base 312 having a pedestal 330, a shaft 332 and a primary housing 334. The primary housing 334 encloses the primary 320 and provides an annular structure for supporting the lamp assembly 314. In the illustrated embodiment, a transparent plate 340 is mounted within the primary housing 334 to receive the lamp assembly 314. The plate 340 defines a central opening 342 to nest the lamp assembly 314. In this embodiment, the lamp assembly 314 is generally "egg-shaped" having a pair of light transmissive housing components disposed on opposite sides of a support ring 360. More specifically, the lamp assembly 314 includes a transparent housing portion 362 and a translucent housing portion 364. A separate light source, such as incandescent bulbs, may be positioned within each housing portion 362 and 364 or a single light source may be provided to cast light through both housing portions 362 and 364. The housing portions 362 and 364 each have an external diameter that is smaller than the internal diameter of the central opening 342 in the plate 340. The external diameter of the support ring 360 is, however, greater than the internal diameter of the central opening 342. As a result, the lamp assembly 314 can be suspended within the central opening 342 upon the support ring 360.

In use, the character of the light emitted by the lamp 300 can be varied by placing the lamp assembly 314 into the central opening 342 in different orientations. In particular, placing the lamp assembly 314 with the transparent housing portion 362 facing downwardly causes the desk lamp 300 to cast bright, clear light onto the surface below, while casting soft, diffuse light upwardly away from the surface. Inverting the lamp assembly 314 and placing it with the translucent housing portion 364 facing downwardly causes the desk lamp 300 to cast soft, diffuse light downwardly onto the surface below, and bright, clear light upwardly away from the surface. Variations in the light cast by the lamp 300 can also be achieved by providing the housing portions 362 and 364 with different physical and optical characteristics. For example, the two housing portions 362 and 364 can be manufactured from different color materials, have different sizes or shapes or be formed with different lens characteristics, such as variations in focus, magnification and diffusion. Alternatively, differences in the light cast by the lamp 300 can be achieved by providing different light sources within housing 362 and 364. For example, the two light sources may have different wattage or be of different lamp types. In one embodiment, housing 362 is manufactured from clear glass or polymer, and contains a white incandescent bulb, while housing 364 is manufactured from a translucent glass or polymer, and contains a blue LED.

If desired, the physical distance between the primary and secondary can also be varied by placing the lamp assembly 314 into the central opening 342 in different positions. If the secondary 324 is axially aligned with the support ring 360, then the secondary 324 will be in substantially the same position with respect to the primary 320 regardless of whether the transparent portion 362 or the translucent portion 364 is facing upwardly. On the other hand, if the secondary coil 324 is axially offset from the support ring 360, the physical distance between the primary 320 and the secondary 324 will vary depending on the orientation of the lamp assembly 314. The secondary 324 can be offset from the support ring 360 in either direction depending on the position in which more light output is desired.

Figure 26:
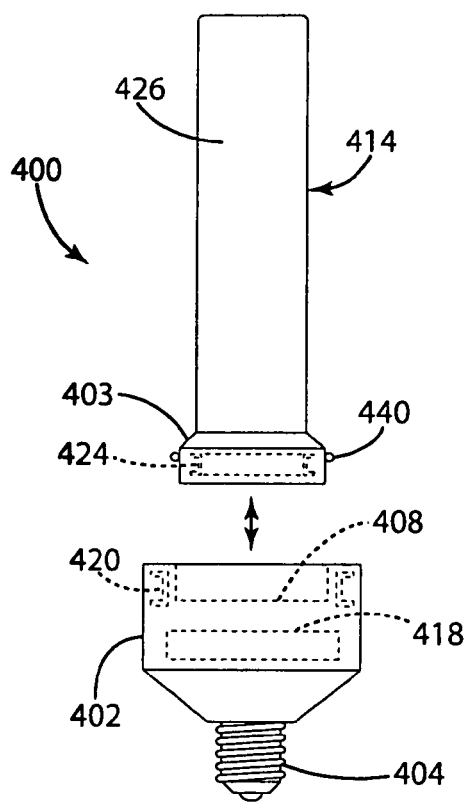
FIG. 26 is a partially exploded side elevational view of replacement lamp base in accordance with an embodiment of the present invention.
Figure 27:
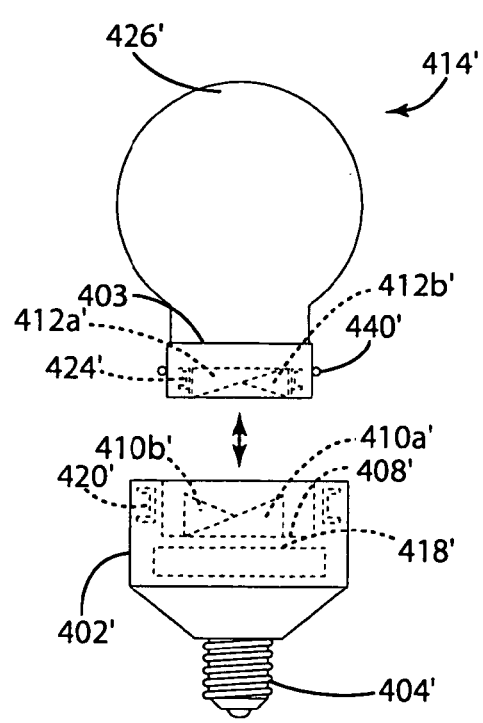
FIG. 27 is a partially exploded side elevational view of an alternative replacement lamp base.
Figure 28:
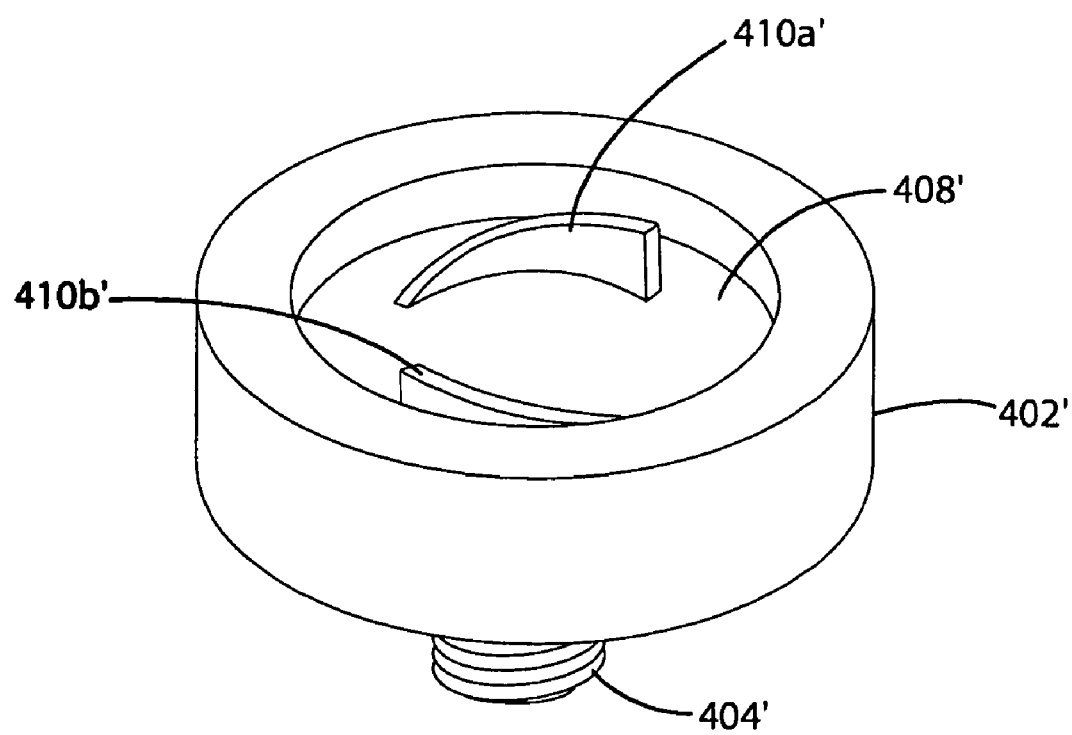
FIG. 28 is a perspective view of a portion of the alternative replacement lamp base of FIG. 27.

In yet another aspect, the present invention is incorporated into a replacement lamp base 400 intended to work in existing screw-base lamps. As shown in FIG. 26, the lamp base 400 includes a housing 402 containing a power supply circuit 418 that drives a primary 420. In the illustrated embodiment, the housing 402 is manufactured from two injection-molded halves that close about the power supply circuit 418 and the primary 420. The housing 402 also includes a screw base 404 that is generally identical to the existing screw-base of conventional incandescent lamps. The screw base 404 is fitted over a lower portion of the housing 402 so that it can be easily screwed into a conventional lamp socket (not shown). Electrical leads (not shown) extend from the screw base 404 to the power supply circuit 418 through corresponding openings in the housing 402. The housing 402 defines a lamp receptacle 408 adapted to receive an inductive lamp assembly 414. The receptacle 408 may include a mechanical dimmer that permits the user to mechanically vary the respective position between the primary and the secondary (See FIGS. 27 and 28). A mechanical dimmer is not, however, necessary, and the receptacle 408 may include a bayonet fitting or other conventional fitting to secure the lamp assembly 414 within the receptacle 408 in a fixed position. In the alternative embodiment shown in FIGS. 27 and 28, the receptacle 408' includes cams 410a-b' that permit the position of the lamp assembly 414' to be mechanically varied. The cams 410a-b' interact with corresponding cams 412a-b' on the undersurface of the secondary housing 403', as described in more detail below. The cams 410a-b' and 412a-b' may be replaced by threads or other similar mechanisms (not shown) for mechanically selectively varying the depth of the lamp assembly 414' within the receptacle 408'. To help to retain the lamp assembly 414 in the desired position within the receptacle 408, the receptacle 408 and the secondary housing 403 are configured to be frictionally interfitted with one another. In this embodiment, a resilient o-ring 440 may be fitted around the secondary housing 403 to provide a firm frictional interface. The o-ring 440 is preferably seating within an annular recess (not shown) to help prevent it from sliding up or down the housing 403. Alternatively, the o-ring 440 may be fitted within an annular recess (not shown) in the receptacle 408. As a further alternative, the mechanical dimmer may include a mechanism for moving the primary 420 within the housing 402 or the secondary 424 within the secondary housing 403. For example, either coil may be slidably movable along its axis within its corresponding housing to vary the distance between the primary and the secondary, or either coil may be pivotally movable within its housing to vary the angular orientation between the primary and the secondary. The power supply circuit 418 may be generally identical to the power supply circuit 18 described above, with component values selected to match the desired light source or range of light sources.

Referring now to FIG. 26, the lamp assembly 414 generally includes a secondary housing 403 that is adapted to be fitted within the lamp receptacle 408, a secondary circuit (not shown) contained within the secondary housing 425, and a light source 426 protruding from the secondary housing 425. The secondary housing 425 generally includes two injection molded halves that are closed around the secondary 424 and the remainder of the secondary circuit (not shown). As noted above, the secondary housing 403' of the alternative embodiment shown in FIG. 27 includes cams 412a-b' on its undersurface to interact with the cams 410a-b' of the receptacle 408. The cams 412a-b' may be eliminated or replaced with other mechanical dimming mechanisms. The secondary circuit is preferably generally identical to the secondary circuit 22 described above, with its component values selected to correspond with the desired light source 426.

Figure 29:
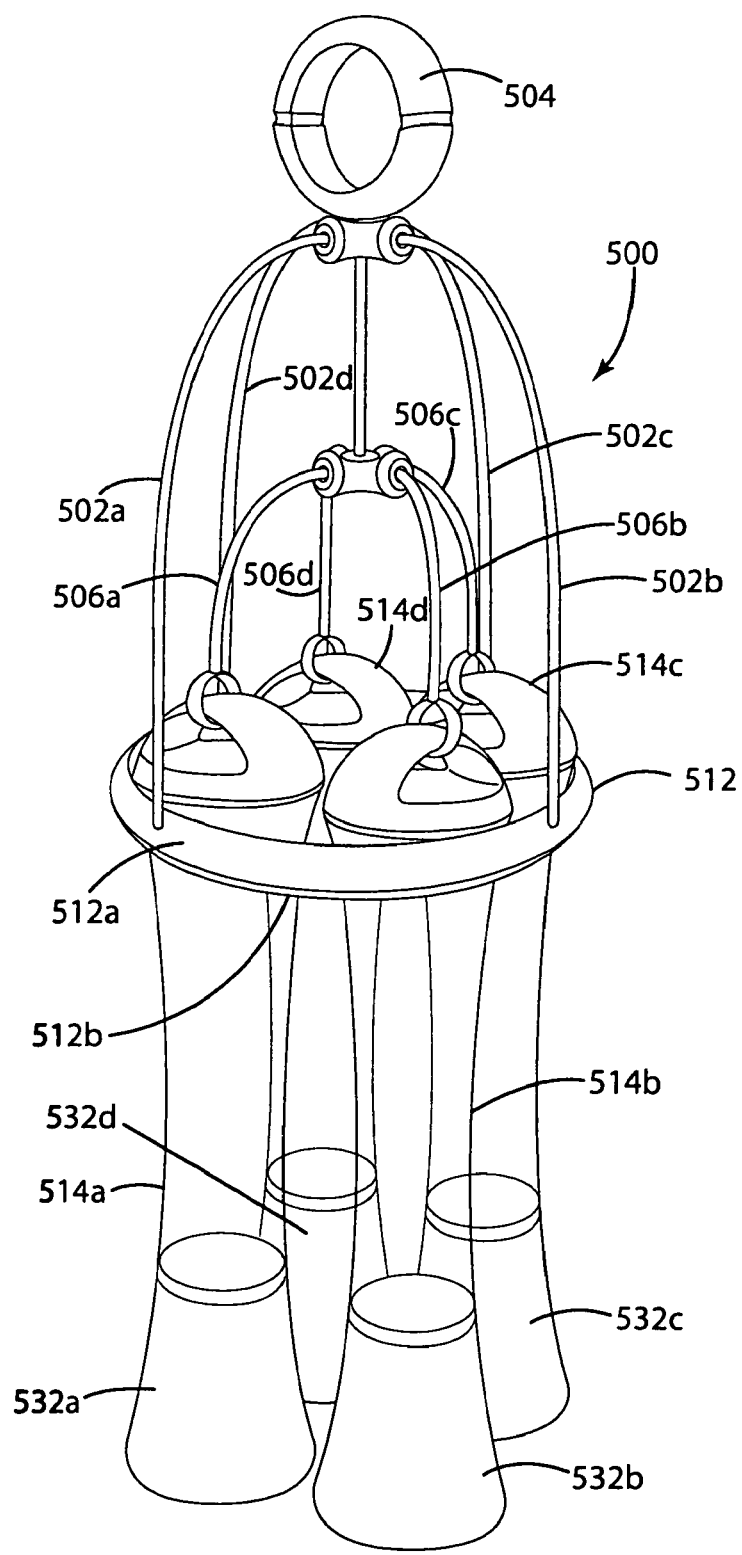
FIG. 29 is a perspective view of a wind chime in accordance with an embodiment of the present invention.
Figures 30, 31:
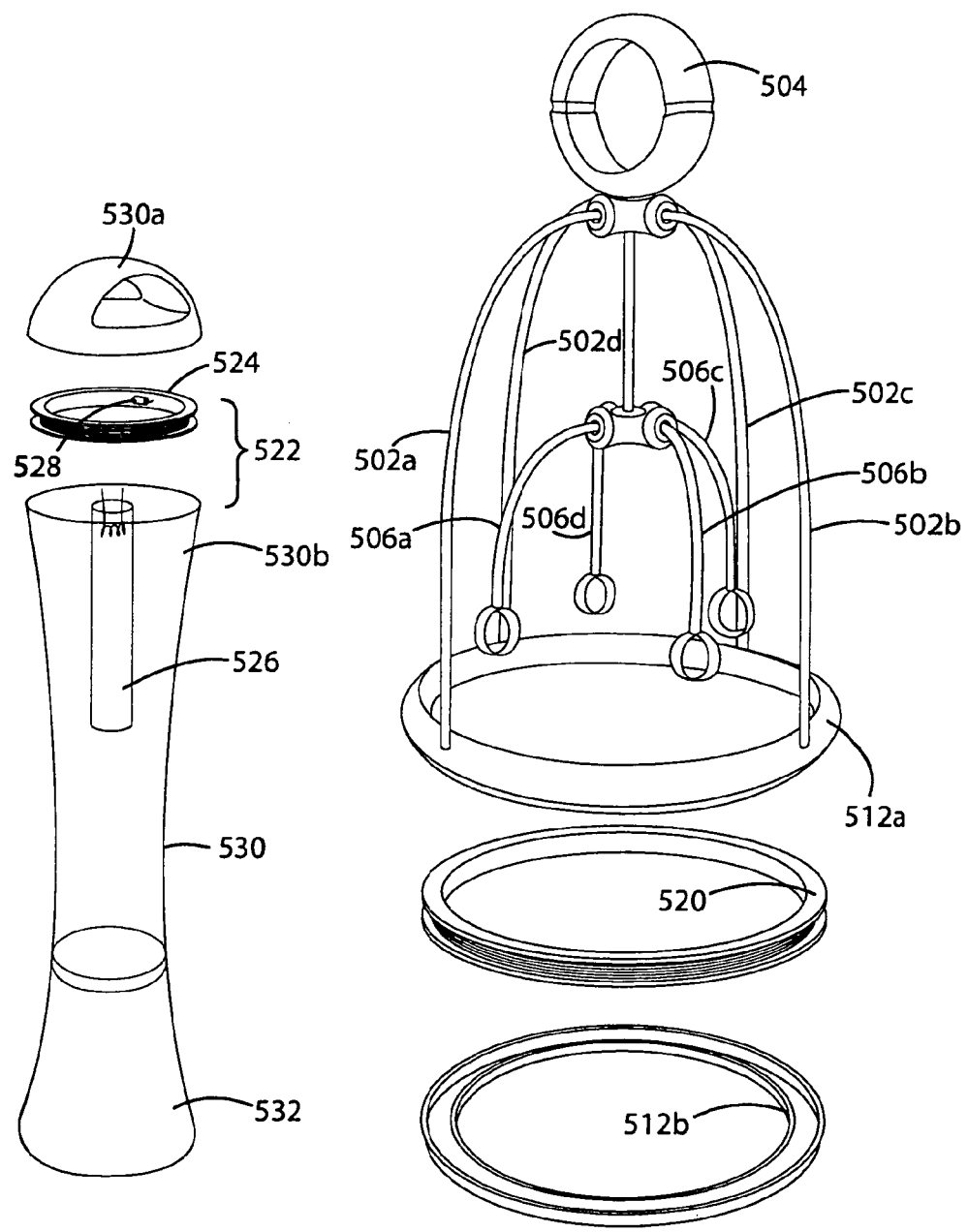
FIG. 30 is a partially exploded perspective view of a portion of the wind chime.
FIG. 31 is a partially exploded perspective view of a chime assembly.
Figure 32:
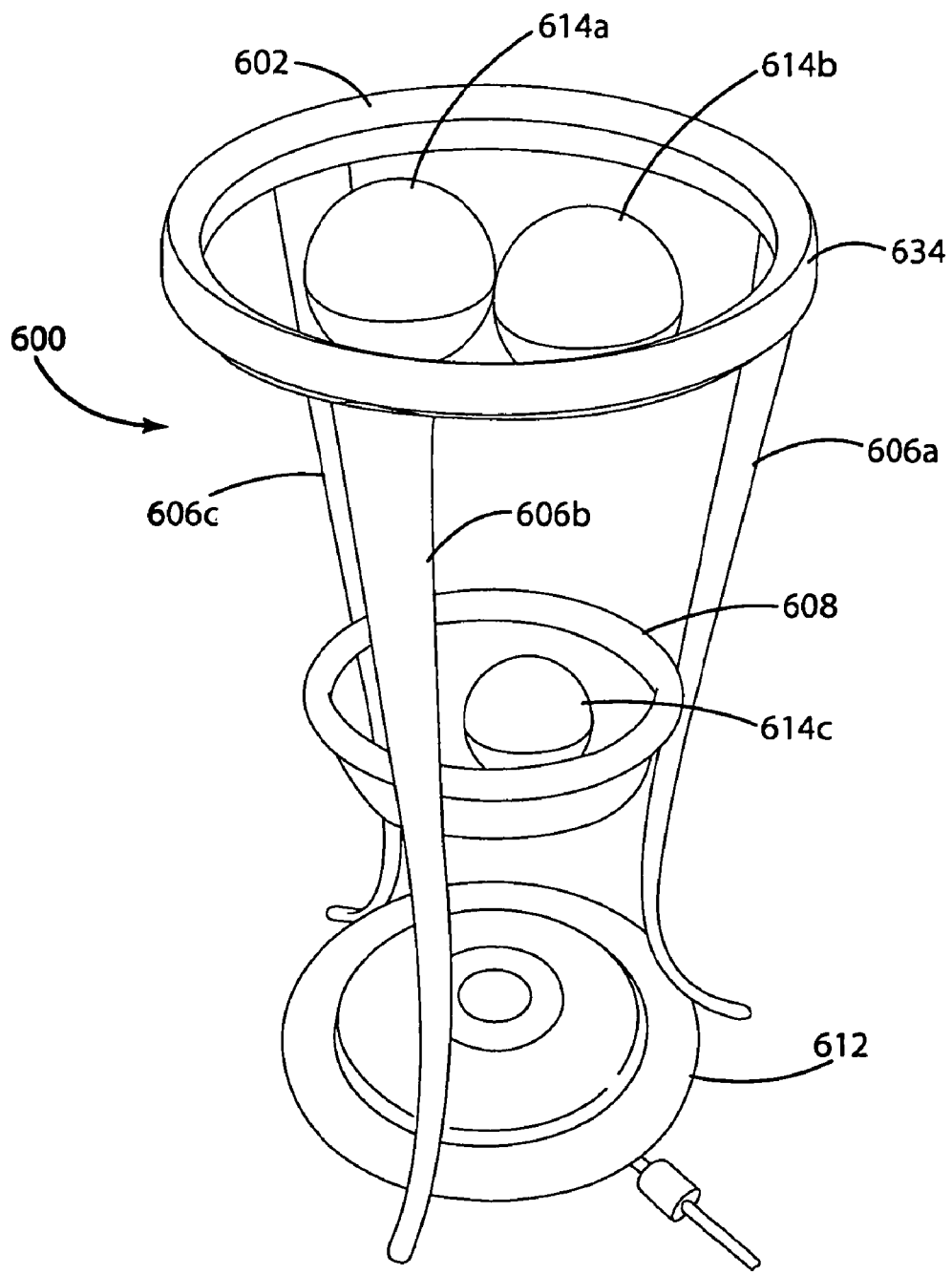
FIG. 32 is a perspective view of a power supply station in accordance with an embodiment of the present invention.

In an alternative embodiment, the present invention is incorporated into inductively powered wind chimes 500 that provide both and audible and visual response to the wind (See FIGS. 29-31). In general, the wind chime 500 includes a primary housing 512 that is suspended from a hanging ring 504 and a plurality of chime assemblies 514a-d that are suspended from the hanging ring 504 within the center of the primary housing 512. The primary housing 512 is suspended from the hanging ring 504 by wires 502a-d or other similar components. The hanging ring 504 is configured to permit the wind chimes 500 to be hung in a wide variety of locations. In the illustrated embodiment, the primary housing 512 includes two injection molded halves 512a-b that house the primary 520 (See FIG. 30). The power supply circuit (not shown) is contained within the wall plug (not shown). The power supply circuit 518 may be generally identical to the power supply circuit 18 described above, with component values selected to match the desired light source or range of light sources.

Each chime assembly 514a-d is suspended within the center of the primary housing 512 by a corresponding wire 506a-d. The separate wires 506a-d permit each chime assembly 514a-d to move freely in response to the wind. Each chime assembly 514a-d generally includes a chime housing 530, a light source 526, a secondary circuit 522 and a chime 532. The chime housing 530 of the illustrated embodiment includes an opaque upper housing portion 530a that is suspended from the corresponding wire 506a-d and a transparent lower housing portion 530b that is mounted to the undersurface of the upper housing portion 530a. The chime housing 530 defines an internal space for containing the secondary circuit 522, including the secondary 524, the light source 526 and any desired capacitor 528. The secondary circuit 522 is housed within the upper portion 530a where it is largely hidden from sight. The light source 526 extends from the upper housing portion 530a down into the lower housing portion 530b. The chime 532 is a generally conventional chime and is mounted to the lower end of each chime housing 530. As a result, as the chime assemblies 514a-d move in the wind, the chimes 532 collide with one another to create sound. At the same time, as each chime assembly 514a-d moves, its secondary 524 moves toward and away from the primary 520. The movement of the secondary 524 within the magnetic field generated by the primary 520 varies the amount of power supplied to the light source 526, and consequently the brightness of the light source 526. More specifically, as a chime assembly 514a-d moves closer to the primary 520, the amount of power transferred by the primary 520 to the secondary 524 increases and the light source 526 becomes brighter. Conversely, as a chime assembly 514a-d moves away from the primary 520, the amount of power transferred to the secondary 524 decreases and the light source 526 becomes dimmer. As a result, increased wind causes increased movement of the chime assembly 514a-d and increased undulations in the brightness of the light sources 526.

Figure 33:
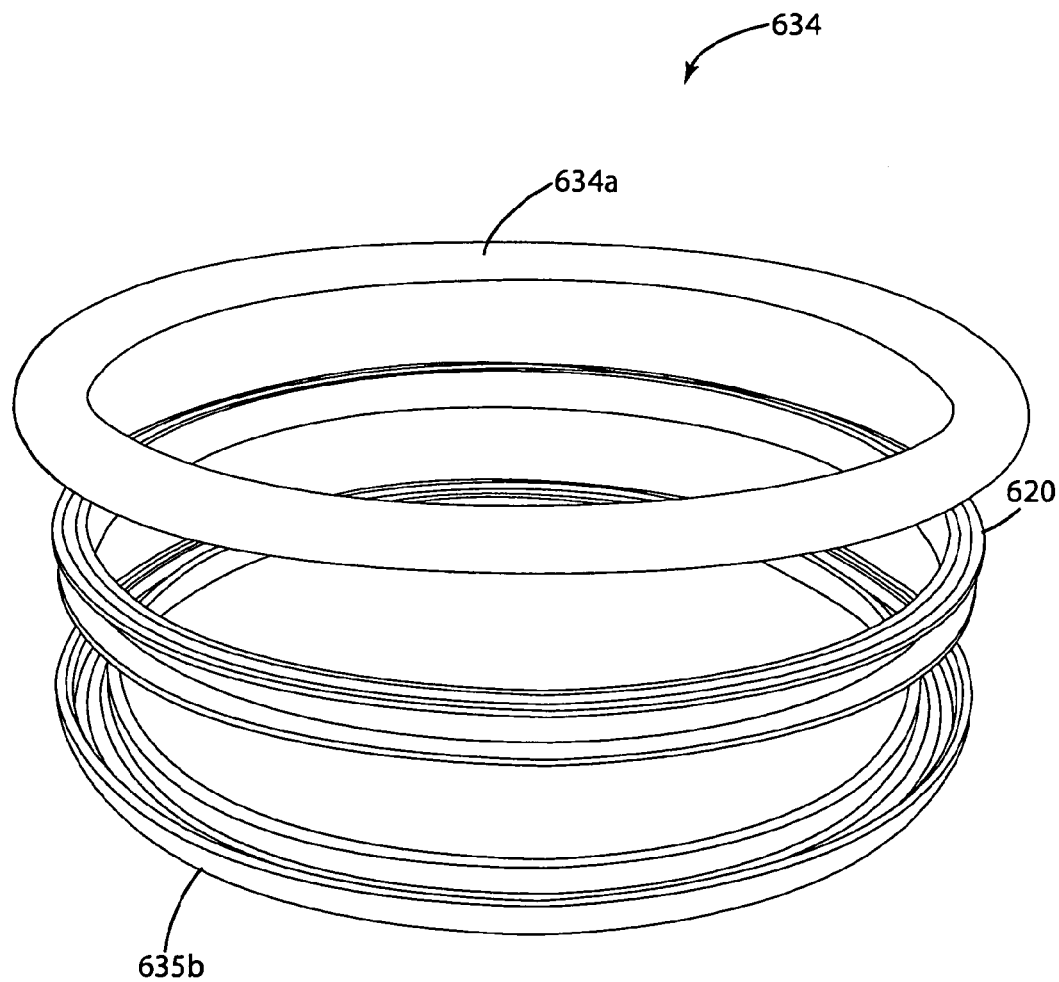
FIG. 33 is a partially exploded perspective view of the primary assembly of the power supply station.

In a further aspect, the present invention relates to an inductive power supply station having a primary that inductively provides power to one or more inductively powered devices, each having its own secondary coil. In the embodiment illustrated in FIGS. 32-35, the inductive power supply station 600 generally includes a power receptacle 602 and a storage receptacle 608 that are supported by a plurality of legs 606a-c. A primary 620 is disposed around the power receptacle 602 to generate a magnetic field that provides inductive power to any inductive devices 650a-c placed within the power receptacle 602. In the described embodiment, the primary 620 has a diameter of 6.5 inches and includes 50 turns of wire 663 wrapped circumferentially around a generally conventional plastic bobbin 633. The wire 663 may be litz wire consisting of eight strands of 32-gauge insulated wire wrapped 1 turn per inch, which may provide the primary 620 with improved efficiency. The primary 620 is contained within primary housing 634. Referring now to FIG. 33, the primary housing 634 includes two annular halves 634a and 634b that enclose the primary 620.

The power receptacle 602 is intended to receive a plurality of inductive devices, such as lamp assemblies 614a-b, at random locations and random orientations. In the illustrated embodiment, the power receptacle 602 is bowl-shaped and is manufactured from a transparent or translucent material, such as glass or plastic. The bowl-shaped power receptacle 602 is fitted within and supported by the primary housing 634. Although the illustrated power receptacle 602 is bowl-shaped, the receptacle may have a variety of alternative constructions. For example, the bowl-shaped receptacle 602 may be replaced by horizontal surface (not shown) upon which inductively powered devices can be placed or it may be replaced by one or more rings from which inductively powered devices can be suspended. As a further example, the receptacle may be a vertical surface adjacent to which various inductive devices can be suspended, such as an inductively powered wall lamp or an inductively powered clock.

As noted above, the illustrated power supply station 600 also includes a storage receptacle 608 mounted to legs 606a-c, for example, by screws or other fasteners. The storage receptacle 608 provides a place for storing lamp assemblies, such as lamp assembly 614c, and other inductively powered devices when they are not in use. In this embodiment, the storage receptacle 608 is bowl-shaped, to complement the shape of the power receptacle 602, and is mounted between the legs 606a-c of the station 600 below the power receptacle 602 and above the base 612. The size, shape, configurations and location of the storage receptacle may vary from application to application as desired. Alternatively, the storage receptacle 608 may be eliminated.

Figure 34:
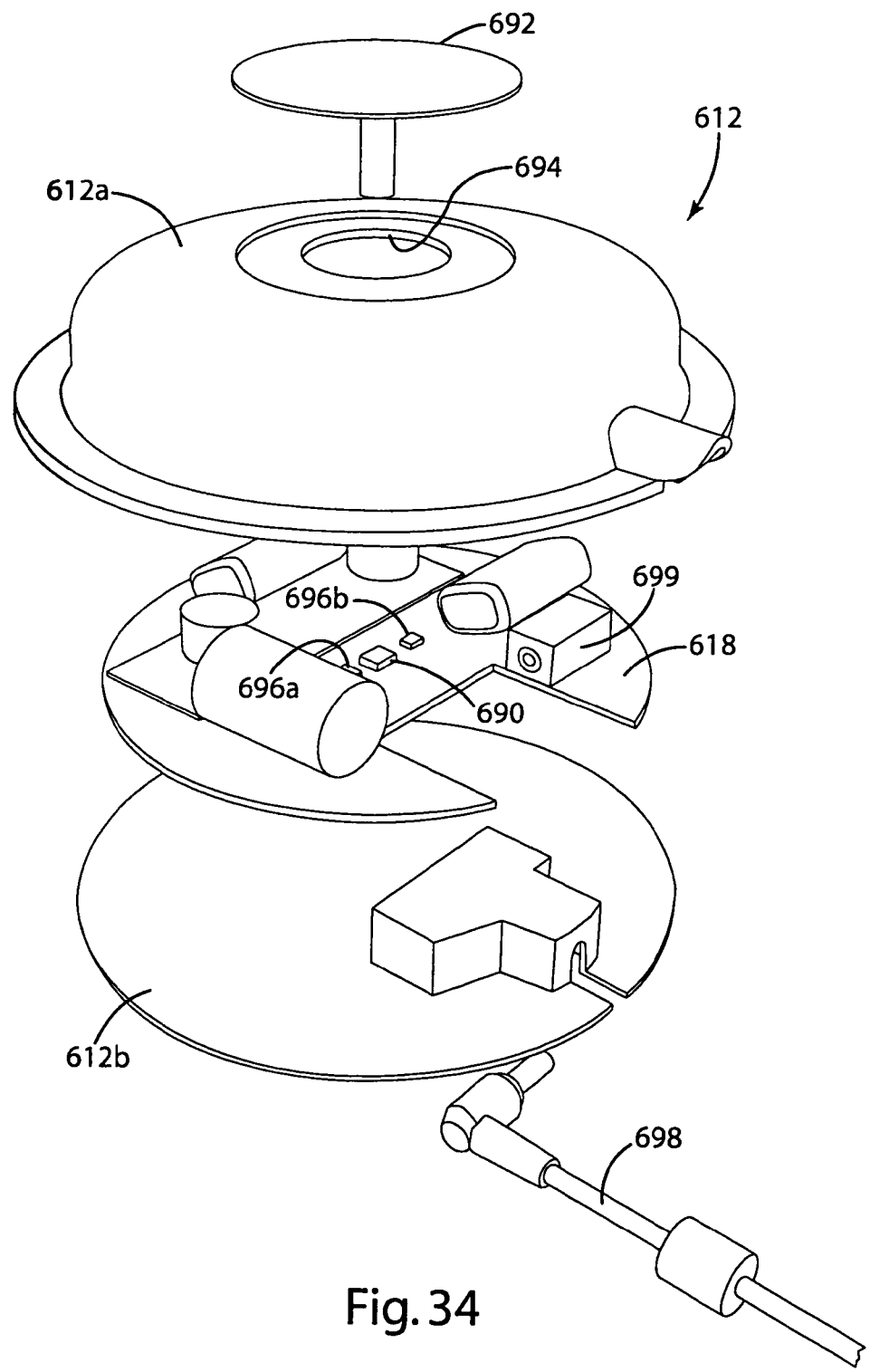
FIG. 34 is a partially exploded perspective view of the base of the power supply station.
Figure 35:
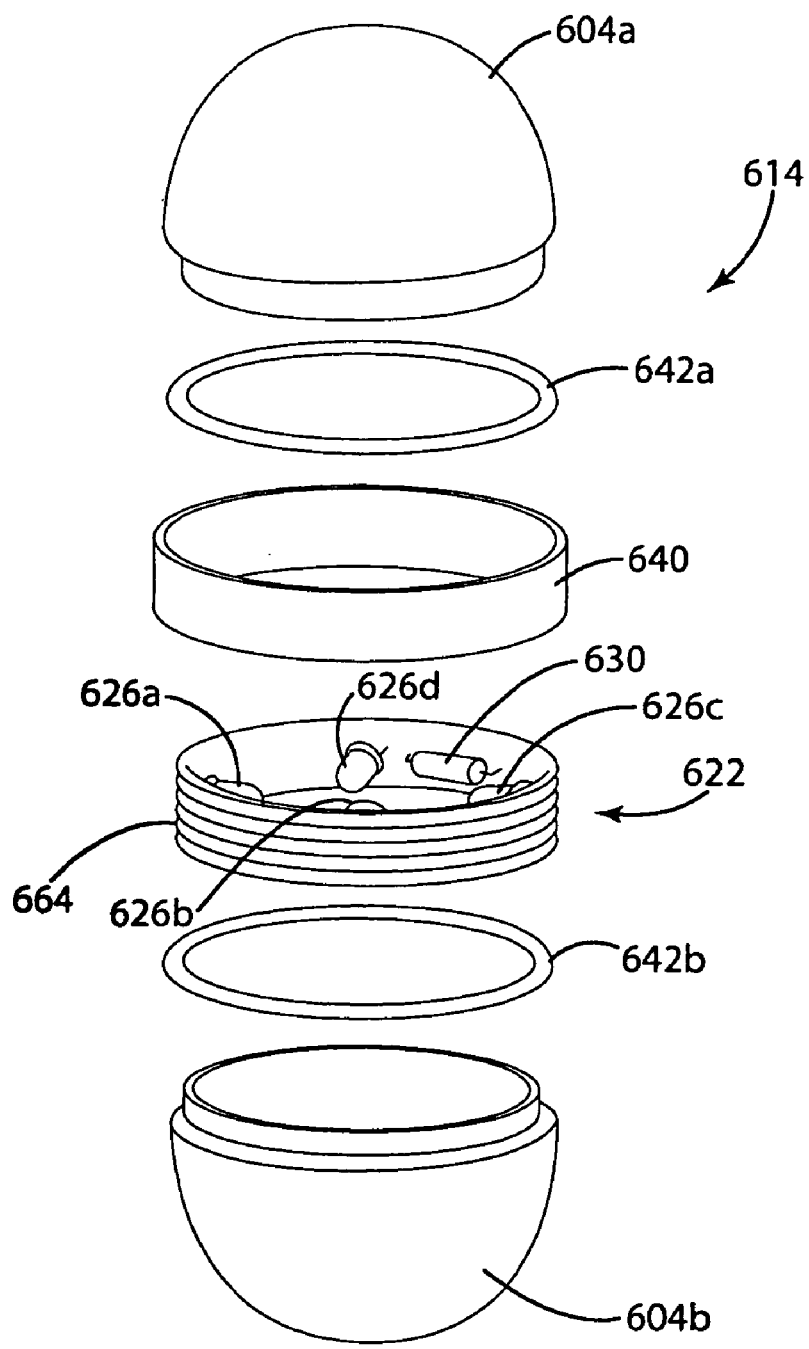
FIG. 35 is a partially exploded perspective view of a lamp assembly in accordance with an embodiment of the present invention.

The power supply station 600 also includes a power supply circuit 618 that supplies power to a primary 620. In the illustrated embodiment, the power supply circuit 618 is disposed within lamp base 612. Referring now to FIG. 34, the lamp base 612 generally includes an upper housing 612a and a lower housing 612b that enclose the power supply circuit 618. The power supply circuit 618 includes a power switch 690 that is actuated by button 692. The button 692 extends down through a corresponding aperture 694 in the upper housing 612a to engage the switch 690. The button 692 may be translucent and the power supply circuit 618 may include a pair of power-indicating LEDs 696a-b that illuminate the button 692 when the power is on. In this embodiment, a power supply cord 698 penetrates the lower housing 612b and is electrically connected to power-in socket 699 to provide AC power to the power supply circuit 618. Electrical leads (not shown) extend from the power supply circuit 618 to the primary 620 through a wiring channel (not shown) in one of the legs 606a-c. The power supply circuit 618 is preferably identical to power supply circuit 18 described above. This power supply circuit 618 has the ability to monitor the power supplied to the primary 620 to determine certain characteristics of the cumulative load (e.g. the inductively powered devices placed in the power receptacle 602), and then to adjust the characteristics of the power supplied to the primary 620 as a function of the monitored values. In one embodiment, the power supply circuit 618 monitors the current supplied to the primary 620 and adjusts the frequency of the power supplied to the primary 610 based on the value of the current.

In the illustrated embodiment, the inductively powered devices are a plurality of lamp assemblies 614a-c. As perhaps best shown in FIG. 35, each of the lamp assemblies 614a-c generally includes a lamp housing 604 that encloses a light source 626a-d and a secondary circuit 622. In this embodiment, the lamp housing 604 is assembled from two glass or injection-molded plastic halves 604a-b, at least one of which is manufactured from a transparent or translucent material. The halves 604a-b are interconnected by cover ring 640, for example, by adhesives or threads. A separate o-ring 642a-b may be fitted between the cover ring 640 and each half 604a-b. The secondary circuit 622 is enclosed within the lamp housing 604, and generally includes a secondary 624 and an optional capacitor 630 that are connected in series with light source 626a-d. In the illustrated embodiment, the light source includes a plurality of LEDs 626a-d. In this embodiment, the secondary 624 has a diameter of 2 inches and includes 27 turns of 26-gauge straight wire 664 wrapped circumferentially around a generally conventional plastic bobbin 662. The characteristics of the secondary 624 (e.g. number of turns, diameter of coil, type of wire) and optional capacitor 630 (e.g. capacitance value) are selected to correspond with the light source 626a-d and the power supplied by the primary 620.

To improve the flexibility of the inductive power supply station, an inductive device may include a secondary having a plurality of coils that are arranged at different orientations. In applications where only a single coil is used, it is possible that a device randomly placed within a power receptacle will be located with the coil oriented substantially parallel to the magnetic field. In such situations, the secondary may not receive sufficient power to power the device from the primary. The use of multiple coils addresses this problem by providing a secondary coil arrangement that significantly increases the likelihood that at least one coil will at least substantially intersect the flux lines of the magnetic field generated by the primary. For example, an inductive device may include a secondary with two coils that are oriented at 90 degrees to one another. With this configuration, at least one of the two coils is likely to extend across the flux lines of the magnetic field and receive power from the primary. The number of separate coils may vary from application to application, for example, the inductive device may include 3, 4, 6 or 8 coils at different orientations to provide improved efficiency in a wide variety of orientations. By providing a sufficient number of coils at different orientations, the inductive device can be configured to receive power from the primary regardless of the orientation of the inductive device.

Figure 36:
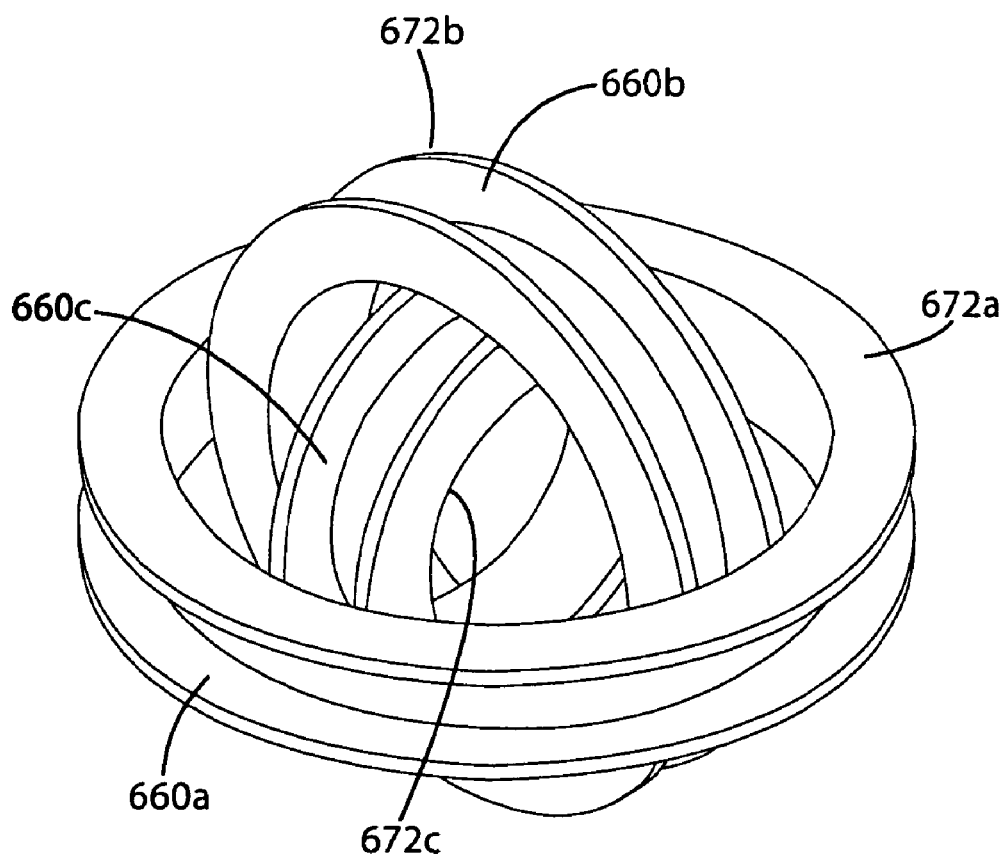
FIG. 36 is a perspective view of a secondary having multiple coils in accordance with an embodiment of the present invention.

In one embodiment, the inductively power device includes a secondary 670 having three separate coils 672a-c; one oriented along each of the x, y and z axes of a Cartesian three-dimensional coordinate system. As shown in FIG. 36, an arrangement of three bobbins 660a-c is provided to receive the three coils 672a-c. The diameters of the three bobbins 660a-c vary so that the bobbins 660a-c can be fitted one within the other. Given that the power induced in a secondary is proportional to the diameter of the secondary, the use of differently sized bobbins may result in an imbalance in the power supplied to each secondary. In applications where it is desirable to balance the power induced in the different coils 672a-c, additional turns of wire can be added to the smaller bobbins 660b-c, with the precise number of additional turns added to each smaller bobbin depending primarily on its size. For example, if the outermost secondary 672a includes seven turns, it may be desirable to include eight turns on the middle secondary 672b and nine turns on the innermost secondary 672c. Alternatively, a spherical bobbin (not shown) can be provided, with each coil being wrapped about the spherical bobbin at the desired location and in the desired orientation, for example, about the x, y and z axes. This embodiment reduces the differences in the diameters of the three secondaries, thereby improving the balance of the coils. Although the secondary with multiple coils is described in connection with the inductively powered lamp assembly 614, a secondary with multiple coils can be incorporated into essentially any inductively power device to maximize power transfer in various orientations of the device within the magnetic field. For example, a cell phone (not shown) or personal digital assistant (not shown) can be provided with an inductively powered battery charger having a secondary with a single coil, such as secondary 622 above, or with multiple coils, such as secondary 670. In this example, a cell phone or personal digital assistant having a secondary with multiple coils can be placed randomly within the power receptacle 602 without concern for its orientation because the secondary 670 will be able to obtain sufficient power to charge the device in any orientation.

Figure 38A:
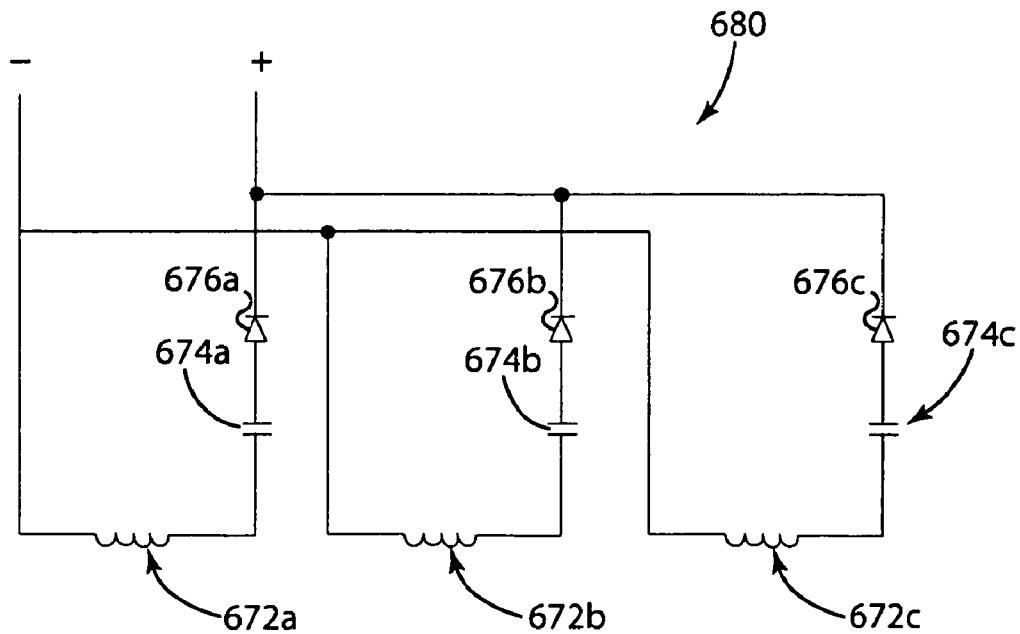
FIG. 38a is a schematic diagram of a secondary circuit for use with a secondary having multiple coils.
Figure 38B:
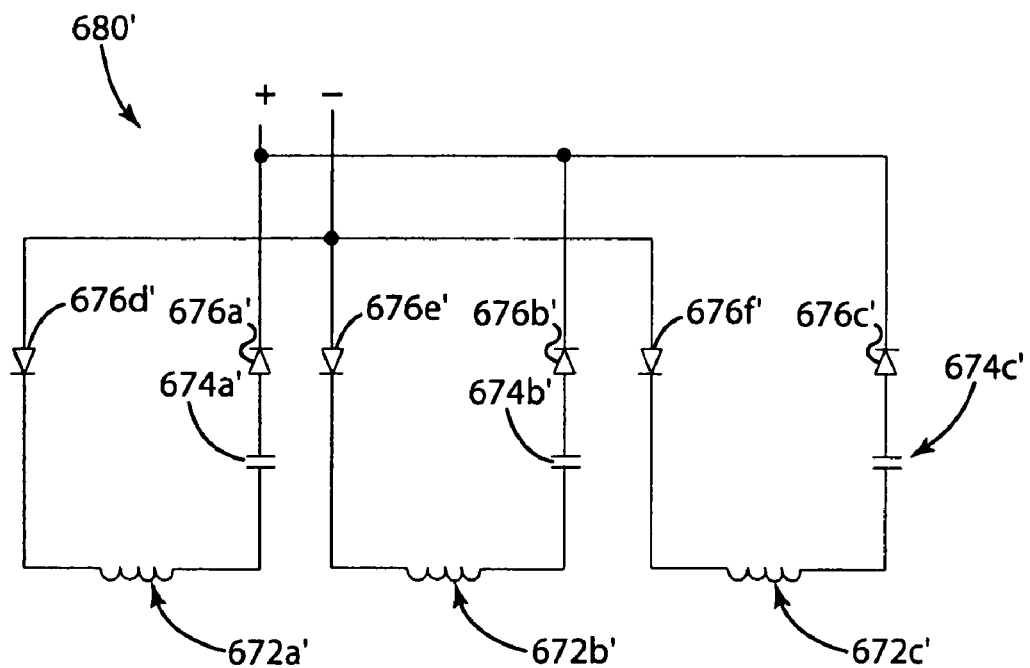
FIG. 38b is a schematic diagram of an alternative secondary circuit for use with a secondary having multiple coils.
Figure 38C:
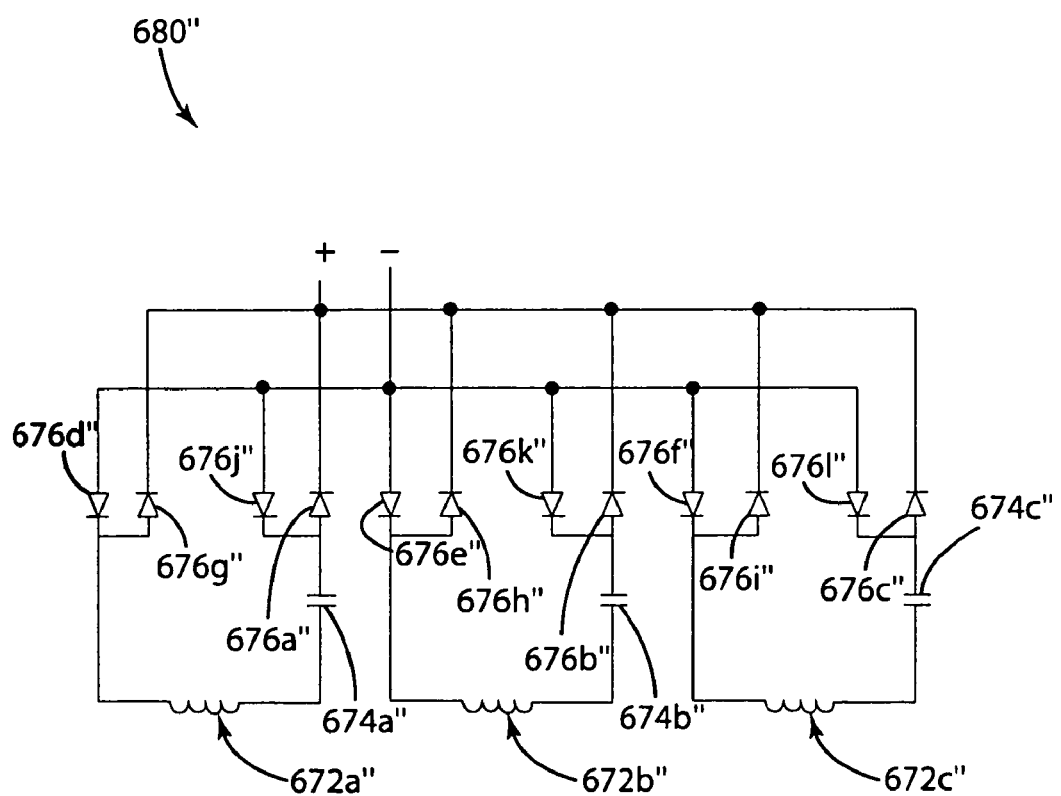
FIG. 38c is a schematic diagram of a second alternative secondary circuit for use with a secondary having multiple coils.

FIGS. 38a-c show circuit diagrams for three embodiments of the three-coil secondary 670. FIG. 38a illustrates a circuit 680 that provides DC power from three separate coils 672a-c. As shown, the three coils 672a-c are connected in parallel to the load, a capacitor 674a-c is connected in series between each coil 672a-c and the load. In this embodiment, the value of each capacitor 674a-c and each diode 676a-c is selected to provide a resonant circuit for the load-side of the circuit. This circuit 680 combines the power induced within each of the coils using the capacitors to provide resonance with the load, and diodes 674a-c rectifying the voltage output from circuit 680. Alternatively, diodes 676a-c can be eliminated from the circuit 680 to provide AC power to the load.

FIG. 38b illustrates a half wave rectifier circuit 680' that provides DC power from three separate coils 672a-c'. As shown, the three coils 672a-c' are connected in parallel to the load through an arrangement of diodes 676a-f is connected in series between each coil 672a-c' and the load. In this embodiment, the value of each diode 676a-f is determined based primarily on the characteristics of the load. Additionally, a capacitor 674a-c' is connected in series between one side of the coil 672a-c' and the corresponding diodes 676a-f. The value of each capacitor 674a-c' is also determined based primarily on the characteristics of the load. This circuit 680' combines the power induced within each of the coils using the capacitors to provide resonance with the load, and diodes 676a-c rectifying the voltage output from the circuit 680'.

FIG. 38c illustrates a full wave rectifier circuit 680" that provides DC power from three separate coils 672a-c'. As shown, the three coils 672a-c' are connected in parallel to the load through an arrangement of diodes 676a-l' is connected in series between each coil 672a-c' and the load. In this embodiment, the value of each diode 676a-l' is determined based primarily on the characteristics of the load. Additionally, a capacitor 674a-c' is connected in series between one side of the coil 672a-c' and the corresponding diodes 676a-l'. The value of each capacitor 674a-c' is determined based primarily on the characteristics of the load. All three of these circuit 680, 680' and 680" perform the function of providing DC power. Circuit 680 is likely the least expensive design, while circuit 680" provides the best control over the DC output, for example, circuit 680" likely provide less fluctuation in the output compared to the other two embodiments.

In use, the illustrated inductive power supply station 600 and accompanying light assemblies 614a-c provide a distinctive and aesthetically pleasing light source. The amount and character of light cast by the system can be adjusted by varying the number of lamp assemblies 614a-c placed within the receptacle 602, by varying the position of each lamp assembly 614a-c and by varying the orientation of each lamp assembly 614a-c within the receptacle. For example, additional lamp assemblies 614a-c can be added to the receptacle to increase the brightness of light cast by the system. Similarly, the location or orientation of a given lamp assembly 614a-c can be varied to control the light output of that particular lamp assembly 614a-c.

Figure 37:
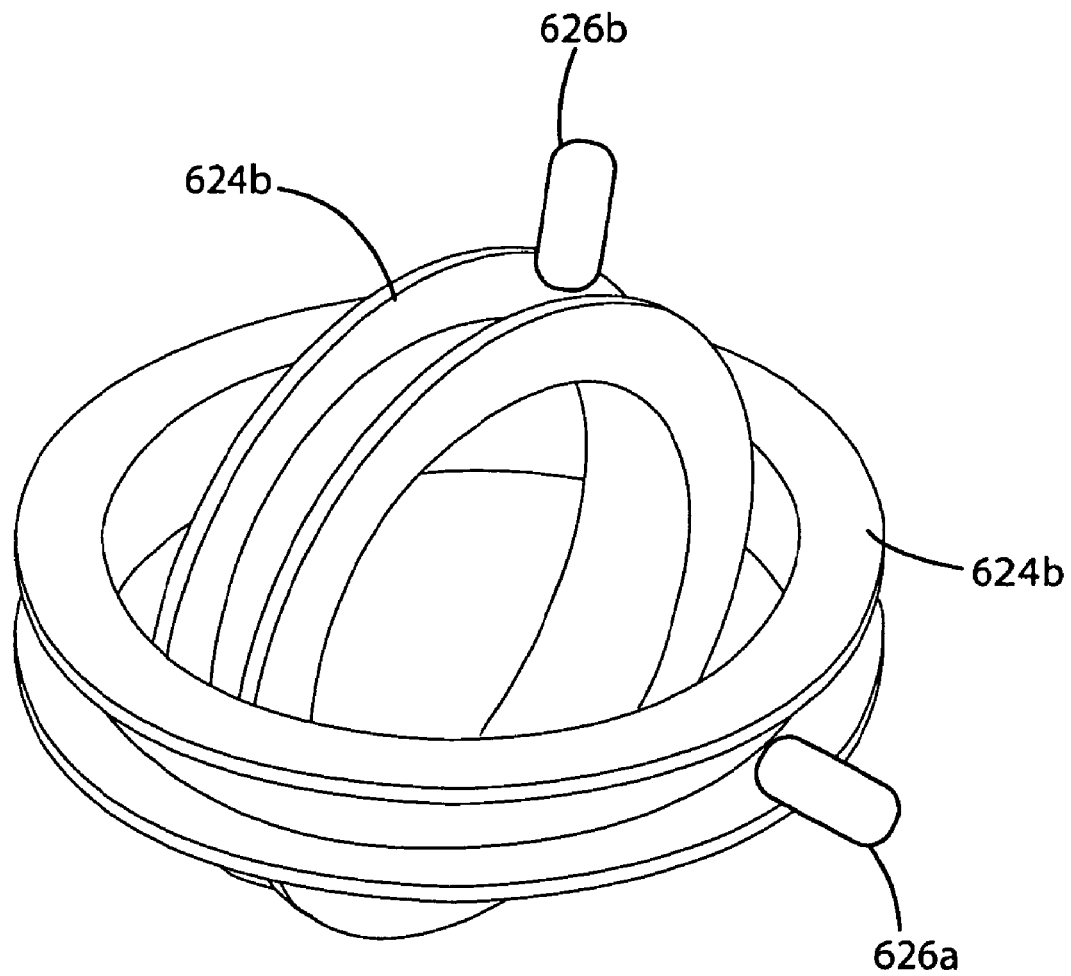
FIG. 37 is a perspective view of an assembly having multiple secondaries in accordance with an embodiment of the present invention.
Figure 39A:
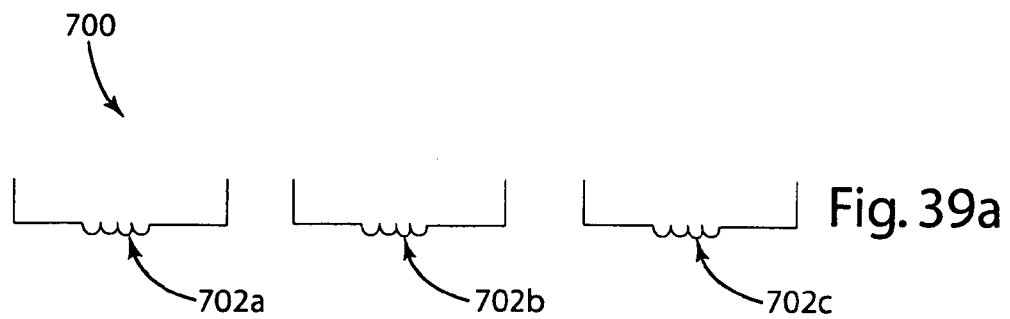
FIG. 39a is a schematic diagram of a circuit for use with an assembly having multiple secondaries.
Figure 39B:
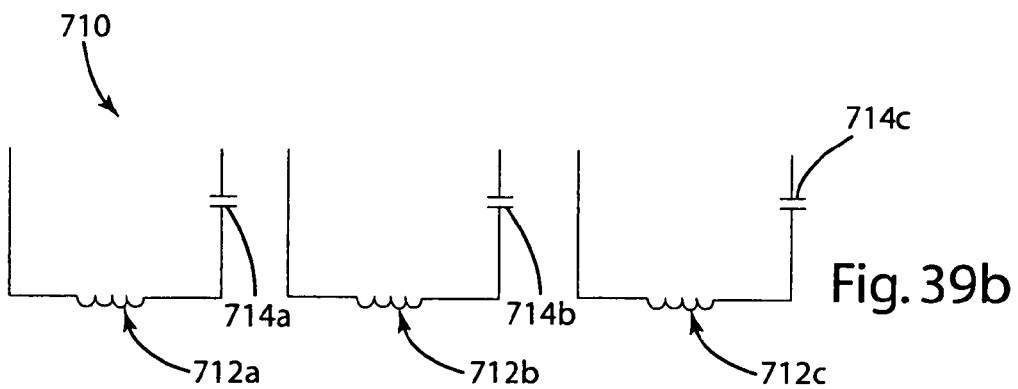
FIG. 39b is a schematic diagram of an alternative circuit for use with an assembly having multiple secondaries.
Figure 39C:
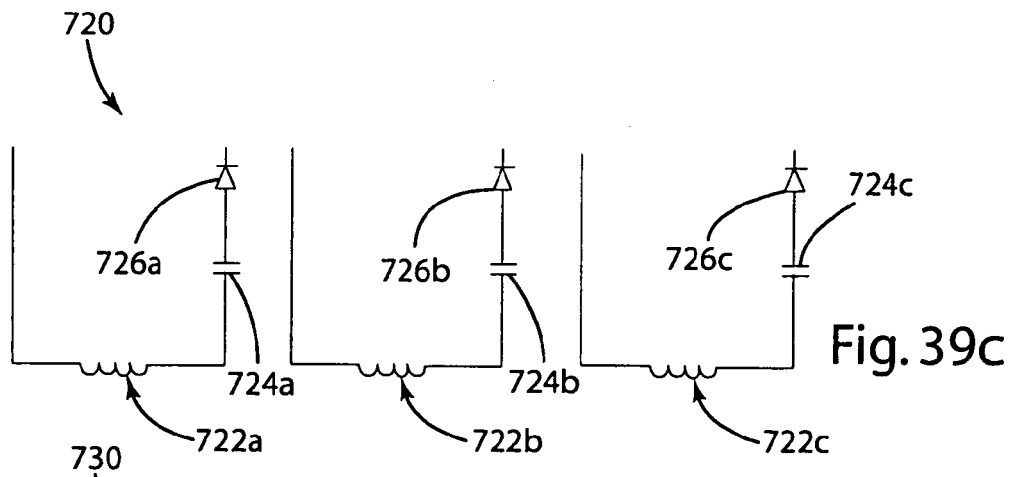
FIG. 39c is a schematic diagram of a second alternative circuit for use with an assembly having multiple secondaries.
Figure 39D:
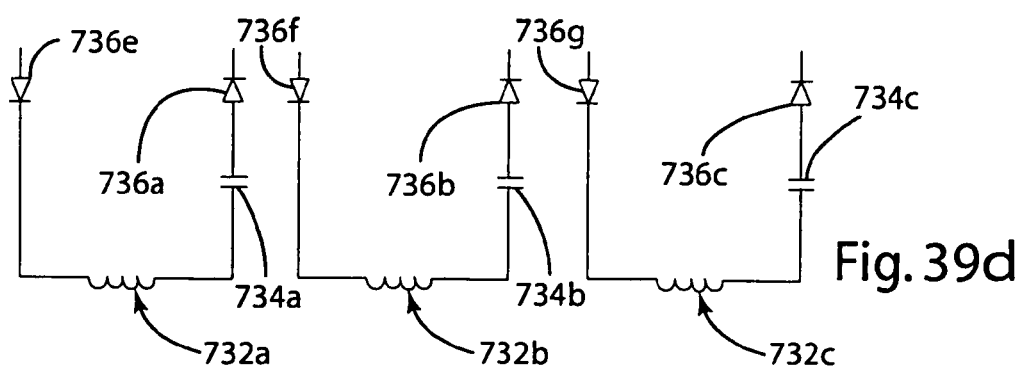
FIG. 39d is a schematic diagram of a third alternative circuit for use with an assembly having multiple secondaries.

In an alternative embodiment, the lamp assembly 614 includes two light sources 626a-b that are connected to separate secondaries 624a-b (See FIG. 37). In this embodiment, the two light sources 626a-b are preferably light emitting diodes, each generating light of a different color. The secondaries 624a-b are oriented 90 degrees from each other so that the power supplied to one secondary is inversely proportional to the power supplied to the other secondary. For example, by rotating the lamp assembly 614 with the power receptacle 602, one secondary is moved into a position that more directly intersects the magnetic field generated by the primary 620 while the other is moved to a position that less directly intersects the magnetic field. As a result, the lamp assembly 614 can be rotated within the power receptacle 602 to selectively control the color of the lamp assembly 614 by adjusting the amount of power supplied to each light source 626a-b. For example, with red and blue light sources, the lamp assembly 614 can be rotated to cast light ranging from pure red through purple to pure blue. If desired, a device can be provided with 3 separate secondaries, each oriented 90 degrees from one another, such as along each of the x, y and z axes of a Cartesian three-dimensional coordinate system. In accordance with this alternative, each secondary can drive a separate light source or power a separate electrical device. It should also be noted that the 3 axis configuration can be used to calculate the orientation of the device by comparing the voltages from each secondary. In some applications, it may be desired to provide an inductively powered device with two sets of coils, a first to set to provide power to one or more devices and a second to provide position information. FIGS. 39a-d illustrate circuit diagrams for various multiple secondary circuits. FIG. 39a illustrates a simple three secondary circuit 700 in which each coil 702a-c is connected to a separate load, such as a light source, a single channel of a three-channel position calculating circuit or other inductively powered device. FIG. 39b illustrates an alternative circuit 710 in which a capacitor 714a-c is connected in series between each secondary 712a-c and its corresponding load. In this embodiment, the capacitance value of each capacitor 714a-c is selected primarily as a function of the corresponding load and the inductance of the corresponding secondary to tune the power within each secondary circuit. FIG. 39c illustrates an alternative circuit 720 in which a capacitor 724a-c and a diode 726a-c are connected in series between each secondary 722a-c and its corresponding load. This circuit 720 provides limited rectification to provide a separate source of DC power to each load. In this embodiment, the capacitance value of each capacitor 724a-c and diode 726a-c is selected primarily as a function of the corresponding load and the inductance of the corresponding secondary. FIG. 39d illustrates an alternative circuit 730 in which a capacitor 734a-c and a pair of diodes 736a-f are connected in series between each secondary 732a-c and its corresponding load. This circuit 730 provides half wave rectification to provide a separate source of DC power to each load. In this embodiment, the capacitance value of each capacitor 724a-c and diode 726a-c is selected primarily as a function of the corresponding load and the inductance of the corresponding secondary. Although not illustrated, each secondary may alternatively include a full wave rectification circuit to provide a separate source of DC power to each load.

Although the inductive power supply station 600 is illustrated in connection with a unique lamp construction, the inductive devices may include other types of inductively powered devices. For example, a cell phone, personal digital assistant or other similar device may include an inductively powered battery charger that is configured to receive power from the inductive power supply station. In such applications, the inductively powered devices can be charged simply by placing it within the power receptacle. The inductively powered device may use the power supplied by the secondary to directly power, rather than simple recharge, the device. For example, a miniature radio, MP3 music player or other media player can be provided with inductive secondary circuits, permitting them to be powered by the power supply station.

The above description is that of a preferred embodiment of the invention. Various alterations and changes can be made without departing from the spirit and broader aspects of the invention as defined in the appended claims, which are to be interpreted in accordance with the principles of patent law including the doctrine of equivalents. Any reference to claim elements in the singular, for example, using the articles "a," "an," "the" or "said," is not to be construed as limiting the element to the singular.

The invention claimed is:

1. A secondary for an inductively powered device comprising:
    a first coil arranged at a first angular orientation for receiving inductive power;
    a second coil arranged at a second angular orientation for receiving inductive power, said first angular orientation being different from said second orientation, wherein said first coil and said second coil are coreless; and a circuit for electrically connecting said first coil and said second coil in parallel with a common load.

2. The secondary of claim 1 wherein said first angular orientation and said second angular orientation are about ninety degrees apart.

3. The secondary of claim 1 further comprising a third coil arranged at a third angular orientation for receiving inductive power, said third angular orientation being different from said first orientation and said second orientation.

4. The secondary of claim 3 wherein said first angular orientation, said second angular orientation and said third angular orientation are each about ninety degrees apart from one another.

5. The secondary of claim 4 further comprising a capacitor connected in series between said load and each of said first coil, said second coil and said third coil.

6. The secondary of claim 3 wherein said first coil, said second coil and said third coil are electrically connected in a half-bridge arrangement with a diode connected in series between said load and each of said first coil, said second coil and said third coil.

7. The secondary of claim 3 wherein said first coil, said second coil and said third coil are electrically connected in a full bridge arrangement with a pair of diodes connected in series between said load and opposite sides of each of said first coil, said second coil and said third coil.

8. The secondary of claim 3 wherein said first coil, said second coil and said third coil are wrapped about a common bobbin.

9. The secondary of claim 3 wherein said first coil, said second coil and said third coil are wrapped about a common substantially spherical bobbin.

10. The secondary of claim 3 wherein said first coil is wrapped about a first bobbin, said second coil is wrapped about a second bobbin and said third coil is wrapped about a third bobbin.

11. The secondary of claim 10 wherein said first bobbin is fitted within said second bobbin and said second bobbin is fitted within said third bobbin.

12. The secondary of claim 10 wherein said first bobbin has a first diameter, said second bobbin has a second diameter and said third bobbin has a third diameter, said first diameter being smaller than said second diameter, said second diameter being smaller than said third diameter; and wherein said first coil includes a greater number of turns than said second coil and said second coil includes a greater number of turns than said third coil.

* * * * *